(12) United States Patent
Porter et al.

(10) Patent No.: US 8,636,511 B2
(45) Date of Patent: Jan. 28, 2014

(54) DENTAL IMPLANT SYSTEM

(75) Inventors: Stephen S. Porter, Palm Beach Gardens, FL (US); Dan P. Rogers, North Palm Beach, FL (US); Ralph E. Goodman, West Palm Beach, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 190 days.

(21) Appl. No.: 12/361,260

(22) Filed: Jan. 28, 2009

(65) Prior Publication Data

US 2009/0136899 A1    May 28, 2009

Related U.S. Application Data

(62) Division of application No. 10/713,328, filed on Nov. 13, 2003, now Pat. No. 7,484,959.

(60) Provisional application No. 60/450,541, filed on Feb. 26, 2003, provisional application No. 60/425,976, filed on Nov. 13, 2002.

(51) Int. Cl.
*A61C 8/00* (2006.01)

(52) U.S. Cl.
USPC .......................................................... 433/174

(58) Field of Classification Search
USPC ................ 433/172–176, 201.1; 623/17.17
See application file for complete search history.

(56) References Cited

U.S. PATENT DOCUMENTS

| | | | |
|---|---|---|---|
| 711,324 A | 10/1902 | Lacy | |
| 3,514,858 A | 6/1970 | Silverman | 32/2 |
| 3,618,212 A | 11/1971 | Weissman | 32/10 A |
| 3,643,658 A | 2/1972 | Steinemenan | 128/92 D |
| 3,726,011 A | 4/1973 | Savignano | 32/10 A |
| 3,760,502 A | 9/1973 | Hirsch | 32/8 |
| 3,777,346 A | 12/1973 | Steinemann | 29/180 |
| 3,919,723 A | 11/1975 | Heimke et al. | 3/1.9 |
| 3,971,135 A | 7/1976 | Leu | 32/48 |
| 4,011,602 A | 3/1977 | Rybicki et al. | |
| 4,040,129 A | 8/1977 | Steinemann et al. | 3/1.9 |
| 4,158,256 A | 6/1979 | Wiland et al. | 32/12 |
| 4,179,810 A | 12/1979 | Kirsch | 433/75 |
| 4,180,910 A | 1/1980 | Straumann et al. | 433/173 |
| 4,185,383 A | 1/1980 | Heimke et al. | 433/173 |
| 4,219,015 A | 8/1980 | Steinemann | 128/92 D |
| 4,234,309 A | 11/1980 | Sellers | 433/225 |

(Continued)

FOREIGN PATENT DOCUMENTS

WO        WO 99/08620        *    2/1999

*Primary Examiner* — Cris L Rodriguez
*Assistant Examiner* — Edward Moran
(74) *Attorney, Agent, or Firm* — Nixon Peabody LLP

(57) ABSTRACT

An implant comprising two internal anti-rotational features. One anti-rotational feature is adapted to engage a driving tools while the other anti-rotational feature is adapted to engage an abutment. An implant abutment system is provided with an angled abutment adapted to mate with one of the anti-rotational features. A second, straight abutment is adapted to engage with the other anti-rotational feature. An abutment is provided with resilient fingers to interface with the implant and provide tactile and audible feedback indicating when the abutment is properly seated. An abutment screw extends through the abutment and engages the implant bore distal of the stem of the abutment. The abutment screw limits axial movement of the abutment relative to the implant. A driving tool comprising one of at least retention structure and visual alignment indicia is provided to facilitate screwing the implant into a patient's bone.

19 Claims, 9 Drawing Sheets

(56) References Cited

U.S. PATENT DOCUMENTS

| | | | |
|---|---|---|---|
| 4,293,302 A | 10/1981 | Hassler et al. | 433/173 |
| 4,324,549 A | 4/1982 | Madray | 433/169 |
| 4,328,593 A | 5/1982 | Sutter et al. | 3/1.91 |
| 4,332,036 A | 6/1982 | Sutter et al. | 3/1.91 |
| 4,380,436 A | 4/1983 | Kipp | 433/182 |
| 4,388,921 A | 6/1983 | Sutter et al. | 128/92 B |
| 4,416,629 A | 11/1983 | Mozsary et al. | 433/174 |
| 4,424,037 A | 1/1984 | Ogino et al. | 433/173 |
| 4,444,310 A | 4/1984 | Odell | 206/366 |
| 4,447,209 A | 5/1984 | Sutter | 433/173 |
| 4,484,570 A | 11/1984 | Sutter et al. | 128/92 D |
| 4,486,178 A | 12/1984 | Schulte | 433/173 |
| 4,490,116 A | 12/1984 | Deutsch et al. | 433/215 |
| 4,540,367 A | 9/1985 | Sulc | 433/181 |
| 4,560,353 A | 12/1985 | Schulte et al. | 433/173 |
| 4,571,185 A | 2/1986 | Rota | 433/173 |
| 4,591,483 A | 5/1986 | Nawaz | 420/463 |
| 4,600,388 A | 7/1986 | Linkow | 433/176 |
| 4,626,214 A | 12/1986 | Artal | 433/174 |
| 4,657,510 A | 4/1987 | Gittleman | 433/173 |
| 4,671,410 A | 6/1987 | Hansson et al. | 206/438 |
| 4,671,768 A | 6/1987 | Ton | 433/174 |
| 4,681,542 A | 7/1987 | Baum | 433/172 |
| 4,687,443 A | 8/1987 | Driskell | 433/173 |
| 4,710,075 A | 12/1987 | Davison | 408/202 |
| 4,712,681 A | 12/1987 | Branemark et al. | 206/438 |
| 4,714,076 A | 12/1987 | Comte et al. | 128/92 ZW |
| 4,715,817 A | 12/1987 | Zuest et al. | 433/181 |
| 4,722,688 A | 2/1988 | Lonca | 433/173 |
| 4,722,733 A | 2/1988 | Howson | 604/411 |
| 4,731,085 A | 3/1988 | Koch | 623/16 |
| 4,744,754 A | 5/1988 | Ross | 433/173 |
| 4,756,691 A | 7/1988 | Pilarek | 433/177 |
| 4,758,161 A | 7/1988 | Niznick | 433/173 |
| 4,759,768 A | 7/1988 | Hermann et al. | 623/21 |
| 4,763,788 A | 8/1988 | Jorneus et al. | 206/438 |
| 4,772,204 A | 9/1988 | Söderberg | 433/174 |
| 4,793,808 A | 12/1988 | Kirsch | 433/173 |
| 4,803,976 A | 2/1989 | Frigg et al. | 128/92 VD |
| 4,824,372 A | 4/1989 | Jorneus et al. | 433/174 |
| 4,826,434 A | 5/1989 | Krueger | 433/174 |
| 4,846,683 A | 7/1989 | Lazzara et al. | |
| 4,850,870 A | 7/1989 | Lazzara et al. | 433/174 |
| 4,850,873 A | 7/1989 | Lazzara et al. | 433/220 |
| 4,854,872 A | 8/1989 | Detsch | 433/173 |
| 4,856,648 A | 8/1989 | Krueger | 206/63.5 |
| 4,856,944 A | 8/1989 | Reinauer | 408/59 |
| 4,856,994 A | 8/1989 | Lazzara et al. | 433/173 |
| 4,872,839 A | 10/1989 | Brajnovic | 433/173 |
| 4,875,475 A | 10/1989 | Comte et al. | 128/924 Y |
| 4,880,006 A | 11/1989 | Albrektsson et al. | 128/630 |
| 4,881,897 A | 11/1989 | Franek et al. | 433/169 |
| 4,906,191 A | 3/1990 | Söderberg | 433/213 |
| 4,906,420 A | 3/1990 | Brajnovic et al. | 264/17 |
| 4,917,703 A | 4/1990 | Albrektsson | 623/66 |
| 4,936,313 A | 6/1990 | Burkhardt et al. | 128/751 |
| 4,955,811 A | 9/1990 | Lazzara et al. | 433/173 |
| 4,960,381 A | 10/1990 | Niznick | 433/174 |
| 4,978,007 A | 12/1990 | Jacobs et al. | 206/469 |
| 4,983,184 A | 1/1991 | Steinemann | 623/66 |
| 4,988,298 A | 1/1991 | Lazzara et al. | 433/173 |
| 4,995,810 A | 2/1991 | Söderberg | 433/141 |
| 5,000,685 A | 3/1991 | Brajnovic | 433/173 |
| 5,002,542 A | 3/1991 | Frigg | 606/61 |
| 5,006,069 A | 4/1991 | Lazzara et al. | 433/173 |
| 5,006,070 A | 4/1991 | Komatsu | 433/176 |
| 5,015,186 A | 5/1991 | Detsch | |
| 5,019,083 A | 5/1991 | Klapper et al. | 606/99 |
| 5,022,860 A | 6/1991 | Lazzara et al. | 433/173 |
| 5,026,285 A | 6/1991 | Durr et al. | 433/173 |
| 5,030,094 A | 7/1991 | Nardi et al. | 433/169 |
| 5,030,096 A | 7/1991 | Hurson et al. | 433/173 |
| 5,035,619 A | 7/1991 | Daftary | 433/173 |
| 5,040,983 A | 8/1991 | Binon | 433/173 |
| 5,045,054 A | 9/1991 | Hood et al. | 604/22 |
| 5,049,072 A | 9/1991 | Lueschen | 433/173 |
| 5,049,073 A | 9/1991 | Lauks | 433/173 |
| 5,049,074 A | 9/1991 | Otani et al. | 433/173 |
| 5,052,930 A | 10/1991 | Lodde et al. | 433/173 |
| 5,052,931 A | 10/1991 | Kirsch | 433/173 |
| 5,061,181 A | 10/1991 | Niznick | 433/174 |
| 5,061,285 A | 10/1991 | Koch | 623/16 |
| 5,062,800 A | 11/1991 | Niznick | 433/229 |
| 5,064,375 A | 11/1991 | Jörnéus | 433/229 |
| 5,069,622 A | 12/1991 | Rangert et al. | 433/173 |
| 5,071,350 A | 12/1991 | Niznick | 433/173 |
| 5,071,351 A | 12/1991 | Green, Jr. et al. | 433/173 |
| 5,073,111 A | 12/1991 | Daftary | 433/173 |
| 5,076,788 A | 12/1991 | Niznick | 433/173 |
| RE33,796 E | 1/1992 | Niznick | 433/173 |
| 5,078,605 A | 1/1992 | Sutter et al. | 433/165 |
| 5,080,685 A | 1/1992 | Bolesky et al. | 623/23 |
| 5,100,323 A | 3/1992 | Friedman et al. | 433/173 |
| 5,105,690 A | 4/1992 | Lazzara et al. | 81/436 |
| 5,106,300 A | 4/1992 | Voitik | 433/173 |
| 5,116,225 A | 5/1992 | Riera | 433/173 |
| 5,120,222 A | 6/1992 | Sulc | 433/181 |
| 5,122,059 A | 6/1992 | Dürr et al. | 433/173 |
| 5,125,840 A | 6/1992 | Dürr et al. | 433/173 |
| 5,125,841 A | 6/1992 | Carlsson et al. | 433/213 |
| 5,135,395 A | 8/1992 | Marlin | 433/174 |
| 5,140,877 A | 8/1992 | Sloan | 81/439 |
| 5,145,371 A | 9/1992 | Jörnéus | 433/173 |
| 5,145,372 A | 9/1992 | Daftary et al. | 433/173 |
| 5,154,612 A | 10/1992 | Carlsson et al. | 433/173 |
| 5,158,458 A | 10/1992 | Perry | 433/141 |
| 5,174,755 A | 12/1992 | Fukuda | 433/173 |
| 5,180,303 A | 1/1993 | Hornburg et al. | 433/173 |
| 5,181,928 A | 1/1993 | Bolesky et al. | 623/23 |
| 5,188,800 A | 2/1993 | Green, Jr. et al. | 422/23 |
| 5,190,543 A | 3/1993 | Schlapfer | 606/61 |
| 5,195,891 A | 3/1993 | Sulc | 433/173 |
| 5,195,892 A | 3/1993 | Gersberg | 433/174 |
| 5,196,016 A | 3/1993 | Buser et al. | 606/72 |
| 5,197,881 A | 3/1993 | Chalifoux | 433/173 |
| 5,199,873 A | 4/1993 | Schulte et al. | 433/174 |
| 5,209,659 A | 5/1993 | Friedman et al. | 433/173 |
| 5,209,666 A | 5/1993 | Balfour et al. | 433/173 |
| 5,211,561 A | 5/1993 | Graub | 433/169 |
| 5,213,500 A | 5/1993 | Salazar et al. | 433/169 |
| 5,213,502 A | 5/1993 | Daftary | 433/172 |
| 5,215,460 A | 6/1993 | Perry | 433/75 |
| 5,238,405 A | 8/1993 | Marlin | 433/173 |
| D339,419 S | 9/1993 | Hood et al. | D24/146 |
| 5,246,368 A | 9/1993 | Sillard | 433/167 |
| 5,246,370 A | 9/1993 | Coatoam | 433/173 |
| D340,981 S | 11/1993 | Hood et al. | D24/146 |
| D341,201 S | 11/1993 | Hood et al. | D24/146 |
| D342,313 S | 12/1993 | Hood et al. | D24/146 |
| 5,281,140 A | 1/1994 | Niznick | 433/172 |
| 5,286,195 A | 2/1994 | Clostermann | 433/172 |
| 5,292,252 A | 3/1994 | Nickerson et al. | 433/173 |
| 5,295,831 A | 3/1994 | Patterson et al. | 433/141 |
| 5,297,963 A | 3/1994 | Dafatry | 433/172 |
| 5,302,125 A | 4/1994 | Kownacki et al. | 433/172 |
| 5,302,126 A | 4/1994 | Wimmer et al. | 433/173 |
| 5,306,149 A | 4/1994 | Schmid et al. | 433/173 |
| 5,312,253 A | 5/1994 | Chalifoux | 433/173 |
| 5,312,254 A | 5/1994 | Rosenlicht | 433/173 |
| 5,312,403 A | 5/1994 | Frigg | 606/54 |
| 5,316,476 A | 5/1994 | Krauser | 433/173 |
| 5,318,570 A | 6/1994 | Hood et al. | 606/99 |
| 5,322,443 A | 6/1994 | Beaty | 433/141 |
| 5,324,297 A | 6/1994 | Hood et al. | 606/99 |
| 5,328,371 A | 7/1994 | Hund et al. | 433/173 |
| 5,334,024 A | 8/1994 | Niznick | 433/173 |
| 5,336,090 A | 8/1994 | Wilson, Jr. et al. | 433/172 |
| 5,338,196 A | 8/1994 | Beaty et al. | 433/172 |
| 5,344,457 A | 9/1994 | Pilliar et al. | 623/16 |
| 5,362,234 A | 11/1994 | Salazar et al. | 433/169 |
| 5,362,237 A | 11/1994 | Chalifoux | |
| 5,368,160 A | 11/1994 | Leuschen et al. | 206/339 |
| 5,368,443 A | 11/1994 | Turkia et al. | 416/184 |
| 5,368,480 A | 11/1994 | Balfour et al. | 433/141 |

(56) References Cited

U.S. PATENT DOCUMENTS

| | | | |
|---|---|---|---|
| 5,368,483 A | 11/1994 | Sutter et al. | 433/173 |
| 5,376,004 A | 12/1994 | Mena | 433/173 |
| 5,387,102 A | 2/1995 | Wagner et al. | 433/173 |
| 5,399,090 A | 3/1995 | Padros-Fradera | |
| 5,403,136 A | 4/1995 | Mathys | 411/310 |
| 5,417,570 A | 5/1995 | Zuest et al. | 433/177 |
| 5,419,702 A | 5/1995 | Beaty et al. | 433/214 |
| 5,431,567 A | 7/1995 | Daftary | 433/172 |
| 5,433,607 A | 7/1995 | Schmid et al. | 433/173 |
| 5,437,550 A | 8/1995 | Beaty et al. | 433/141 |
| 5,437,551 A | 8/1995 | Chalifoux | 433/173 |
| 5,447,434 A | 9/1995 | Shaw | 433/173 |
| 5,449,291 A | 9/1995 | Lueschen et al. | 433/173 |
| 5,452,219 A | 9/1995 | Dehoff et al. | 364/474.05 |
| 5,456,723 A | 10/1995 | Steinemann et al. | 623/16 |
| 5,462,436 A | 10/1995 | Beaty | 433/141 |
| 5,468,150 A | 11/1995 | Brammann | 433/173 |
| 5,476,383 A | 12/1995 | Beaty et al. | 433/214 |
| 5,489,210 A | 2/1996 | Hanosh | 433/173 |
| 5,492,471 A | 2/1996 | Singer | 433/172 |
| 5,502,087 A | 3/1996 | Tateosian et al. | 523/115 |
| 5,520,689 A | 5/1996 | Schläpfer et al. | 606/61 |
| 5,527,182 A | 6/1996 | Willoughby | 433/172 |
| 5,538,426 A | 7/1996 | Harding et al. | 433/172 |
| 5,538,428 A | 7/1996 | Staubli | 433/173 |
| 5,554,028 A | 9/1996 | Hare et al. | 433/214 |
| 5,556,280 A | 9/1996 | Pelak | 433/172 |
| 5,562,448 A | 10/1996 | Mushabac | 433/215 |
| 5,562,733 A | 10/1996 | Weissbach et al. | 623/16 |
| 5,564,921 A | 10/1996 | Marlin | 433/172 |
| 5,564,924 A | 10/1996 | Kwan | 433/173 |
| 5,567,155 A | 10/1996 | Hansen | 433/172 |
| 5,569,035 A | 10/1996 | Balfour et al. | 433/165 |
| 5,571,188 A | 11/1996 | Ellingsen et al. | 623/16 |
| 5,582,299 A | 12/1996 | Lazzara et al. | 206/63.5 |
| 5,588,838 A | 12/1996 | Hansson et al. | 433/173 |
| 5,591,029 A | 1/1997 | Zuest | 433/173 |
| 5,605,457 A | 2/1997 | Bailey et al. | 433/174 |
| 5,607,304 A | 3/1997 | Bailey et al. | 433/174 |
| 5,626,227 A | 5/1997 | Wagner et al. | 206/369 |
| 5,628,630 A | 5/1997 | Misch et al. | 433/174 |
| 5,630,717 A | 5/1997 | Zuest et al. | 433/172 |
| 5,636,989 A | 6/1997 | Somborac et al. | 433/173 |
| 5,651,675 A | 7/1997 | Singer | 433/172 |
| 5,658,147 A | 8/1997 | Phimmasone | 433/213 |
| 5,660,545 A | 8/1997 | Bailey et al. | 433/173 |
| 5,662,476 A | 9/1997 | Ingber et al. | 433/213 |
| 5,667,384 A | 9/1997 | Sutter et al. | 433/172 |
| 5,674,069 A | 10/1997 | Osorio | 433/172 |
| 5,674,071 A | 10/1997 | Beaty et al. | 433/172 |
| 5,674,072 A | 10/1997 | Moser et al. | 433/173 |
| 5,674,073 A | 10/1997 | Ingber et al. | 433/213 |
| 5,674,244 A | 10/1997 | Mathys | 606/208 |
| 5,678,995 A | 10/1997 | Kirsch et al. | 433/169 |
| 5,681,167 A | 10/1997 | Lazarof | 433/174 |
| 5,685,715 A | 11/1997 | Beaty et al. | 433/173 |
| 5,688,123 A | 11/1997 | Meiers et al. | 433/173 |
| 5,692,904 A | 12/1997 | Beaty et al. | 433/143 |
| 5,695,335 A * | 12/1997 | Haas et al. | 433/173 |
| 5,704,788 A | 1/1998 | Milne | 433/173 |
| 5,725,377 A | 3/1998 | Lemler et al. | 433/173 |
| 5,730,598 A | 3/1998 | Story et al. | 433/201.1 |
| 5,733,122 A | 3/1998 | Gordon | 433/172 |
| 5,733,123 A | 3/1998 | Blacklock et al. | 433/172 |
| 5,734,113 A | 3/1998 | Vogt et al. | 73/862.23 |
| 5,741,253 A | 4/1998 | Michelson | 606/61 |
| 5,749,731 A | 5/1998 | Morgan et al. | 433/173 |
| 5,752,830 A | 5/1998 | Suarez | 433/173 |
| 5,752,831 A | 5/1998 | Padros-Fradera | 433/173 |
| 5,755,574 A | 5/1998 | D'Alise | 433/173 |
| 5,755,807 A | 5/1998 | Anstaett et al. | 623/23 |
| 5,759,033 A | 6/1998 | Elia | 433/173 |
| 5,759,034 A | 6/1998 | Daftary | 433/173 |
| 5,759,036 A | 6/1998 | Hinds | 433/214 |
| 5,762,500 A | 6/1998 | Lazarof | 433/213 |
| 5,762,541 A | 6/1998 | Heath et al. | 451/48 |
| 5,766,009 A | 6/1998 | Jeffcoat | 433/173 |
| 5,779,480 A | 7/1998 | Groll et al. | 433/173 |
| 5,782,637 A | 7/1998 | Cosenza | 433/173 |
| 5,782,918 A | 7/1998 | Klardie et al. | 623/16 |
| 5,785,525 A | 7/1998 | Weissman | 433/174 |
| 5,810,589 A | 9/1998 | Michnick et al. | 433/169 |
| 5,810,590 A | 9/1998 | Fried et al. | 433/172 |
| 5,816,812 A | 10/1998 | Kownacki et al. | |
| 5,820,374 A | 10/1998 | Simmons et al. | 433/173 |
| 5,823,776 A | 10/1998 | Duerr et al. | 433/173 |
| 5,823,777 A | 10/1998 | Misch et al. | 433/174 |
| 5,827,062 A | 10/1998 | Driskell et al. | 433/173 |
| D401,695 S | 11/1998 | Daftary | D24/155 |
| 5,829,977 A | 11/1998 | Rogers et al. | 433/172 |
| 5,829,981 A | 11/1998 | Ziegler | 433/214 |
| 5,836,768 A | 11/1998 | Hüskens et al. | 433/173 |
| 5,842,865 A | 12/1998 | Bassett et al. | 433/174 |
| 5,858,253 A | 1/1999 | Holm | 210/702 |
| D405,179 S | 2/1999 | Kirsch et al. | D24/154 |
| 5,865,622 A | 2/1999 | Aleksey | 433/177 |
| 5,871,358 A | 2/1999 | Ingber et al. | 433/213 |
| 5,871,504 A | 2/1999 | Eaton et al. | 606/232 |
| 5,882,200 A | 3/1999 | Sutter et al. | 433/173 |
| 5,888,218 A | 3/1999 | Folsom | 623/16 |
| 5,897,320 A | 4/1999 | Gittleman | 433/180 |
| D410,083 S | 5/1999 | Broberg et al. | D24/156 |
| 5,899,940 A | 5/1999 | Carchidi et al. | 623/16 |
| 5,904,483 A | 5/1999 | Wade | 433/173 |
| 5,906,488 A | 5/1999 | Kvarnström | 433/116 |
| 5,915,968 A | 6/1999 | Kirsch et al. | 433/173 |
| 5,927,979 A | 7/1999 | Misch et al. | 433/173 |
| 5,931,674 A | 8/1999 | Hanosh et al. | 433/173 |
| 5,938,443 A | 8/1999 | Lazzara et al. | 433/173 |
| 5,938,444 A | 8/1999 | Hansson et al. | 433/174 |
| 5,938,446 A | 8/1999 | Andersson et al. | 433/223 |
| 5,944,526 A | 8/1999 | Liu | 433/176 |
| D414,556 S | 9/1999 | Broberg et al. | D24/156 |
| 5,947,733 A | 9/1999 | Sutter et al. | 433/173 |
| 5,947,734 A | 9/1999 | Hanel | 433/173 |
| 5,947,736 A | 9/1999 | Behrend | 433/214 |
| 5,951,287 A | 9/1999 | Hawkinson | 433/173 |
| 5,951,288 A | 9/1999 | Sawa | 433/173 |
| 5,952,399 A | 9/1999 | Rentsch | 523/116 |
| 5,954,504 A | 9/1999 | Misch et al. | 433/174 |
| 5,954,505 A | 9/1999 | Ford | 433/177 |
| 5,961,328 A | 10/1999 | Somborac et al. | |
| 5,961,329 A | 10/1999 | Stucki-McCormick | 433/173 |
| 5,964,591 A | 10/1999 | Beaty et al. | 433/173 |
| 5,975,902 A | 11/1999 | Emmanuel | 433/173 |
| 5,979,643 A | 11/1999 | Blonder et al. | 206/63.5 |
| 5,984,680 A | 11/1999 | Rogers | 433/173 |
| 5,989,028 A | 11/1999 | Niznick | 433/173 |
| 5,989,029 A | 11/1999 | Osorio et al. | 433/173 |
| 5,993,211 A | 11/1999 | Broberg | 433/172 |
| 5,993,214 A | 11/1999 | Persson | 433/223 |
| 6,007,337 A | 12/1999 | Bauer | 433/173 |
| 6,012,923 A | 1/2000 | Bassett et al. | 433/172 |
| 6,030,219 A | 2/2000 | Zuest et al. | 433/181 |
| 6,033,218 A | 3/2000 | Bergstrom et al. | 433/72 |
| 6,036,491 A | 3/2000 | Hansson | 433/174 |
| 6,039,568 A | 3/2000 | Hinds | 433/175 |
| 6,045,361 A | 4/2000 | Misch et al. | 433/214 |
| 6,048,204 A | 4/2000 | Klardie et al. | 433/174 |
| 6,053,733 A | 4/2000 | Aspichueta et al. | 433/173 |
| 6,053,920 A | 4/2000 | Carlsson et al. | 606/72 |
| 6,066,274 A | 5/2000 | Antonson et al. | 264/16 |
| 6,068,478 A | 5/2000 | Grande et al. | 433/172 |
| 6,068,479 A | 5/2000 | Kwan | 433/173 |
| 6,068,480 A | 5/2000 | Misch et al. | 433/173 |
| 6,076,660 A | 6/2000 | Day | 206/63.5 |
| 6,083,004 A | 7/2000 | Misch et al. | 433/173 |
| 6,086,371 A | 7/2000 | Bassett et al. | 433/173 |
| 6,093,023 A | 7/2000 | Sala Meseguer | 433/173 |
| 6,099,311 A | 8/2000 | Wagner et al. | 433/163 |
| 6,102,702 A | 8/2000 | Folsom, Jr. et al. | 433/172 |
| 6,116,904 A | 9/2000 | Kirsch et al. | 433/173 |
| 6,120,292 A | 9/2000 | Buser et al. | 433/173 |
| 6,142,782 A | 11/2000 | Lazarof | 433/174 |

(56) References Cited

U.S. PATENT DOCUMENTS

| | | | |
|---|---|---|---|
| 6,146,387 A | 11/2000 | Trott et al. | 606/104 |
| 6,149,432 A | 11/2000 | Shaw et al. | 433/174 |
| 6,149,433 A | 11/2000 | Ziegler et al. | 433/214 |
| 6,155,828 A | 12/2000 | Lazzara et al. | 433/173 |
| 6,159,008 A | 12/2000 | Kumar | 433/141 |
| 6,159,244 A | 12/2000 | Suddaby | 623/17.11 |
| 6,168,436 B1 | 1/2001 | O'Brien | 433/173 |
| 6,193,516 B1 | 2/2001 | Story | 433/173 |
| 6,196,842 B1 | 3/2001 | Jörnéus | 433/174 |
| 6,203,323 B1 | 3/2001 | Beaty et al. | 433/173 |
| 6,206,696 B1 | 3/2001 | Day | 433/141 |
| 6,208,813 B1 | 3/2001 | Carlsson et al. | 396/324 |
| 6,213,773 B1 | 4/2001 | Gittleman | 433/172 |
| 6,217,331 B1 | 4/2001 | Rogers et al. | 433/173 |
| 6,217,332 B1 | 4/2001 | Kumar | 433/173 |
| 6,220,860 B1 | 4/2001 | Hansson | 433/173 |
| 6,227,858 B1 | 5/2001 | Lundgren | 433/173 |
| 6,227,859 B1 | 5/2001 | Sutter | 433/173 |
| 6,231,342 B1 | 5/2001 | Osorio et al. | 433/173 |
| 6,247,933 B1 | 6/2001 | Wagner et al. | 433/173 |
| 6,254,387 B1 | 7/2001 | Bergström et al. | 433/49 |
| 6,257,890 B1 | 7/2001 | Khoury et al. | 433/174 |
| 6,261,097 B1 | 7/2001 | Schmutz et al. | 433/173 |
| 6,261,098 B1 | 7/2001 | Persson | 433/213 |
| D446,859 S | 8/2001 | Hurson | D24/156 |
| 6,273,720 B1 | 8/2001 | Spalten | 433/173 |
| 6,273,722 B1 | 8/2001 | Phillips | 433/174 |
| 6,276,938 B1 | 8/2001 | Jörneus et al. | 433/172 |
| 6,280,195 B1 | 8/2001 | Broberg et al. | 433/201.1 |
| 6,283,752 B1 | 9/2001 | Kumar | 433/172 |
| 6,283,755 B1 | 9/2001 | Bergström et al. | 433/193 |
| 6,287,119 B1 | 9/2001 | van Nifterick et al. | 433/213 |
| 6,290,499 B1 | 9/2001 | Lazzara et al. | 433/173 |
| 6,290,500 B1 | 9/2001 | Morgan et al. | 433/173 |
| 6,305,938 B1 | 10/2001 | Brånemark | 433/173 |
| 6,305,939 B1 | 10/2001 | Dawood | 433/174 |
| 6,312,260 B1 | 11/2001 | Kumar et al. | 433/174 |
| 6,315,562 B1 | 11/2001 | Kumar | 433/173 |
| 6,315,563 B1 | 11/2001 | Sager | 433/173 |
| 6,332,777 B1 | 12/2001 | Sutter | 433/173 |
| 6,343,930 B1 | 2/2002 | Beaty et al. | 433/173 |
| 6,350,126 B1 | 2/2002 | Levisman | 433/173 |
| 6,358,050 B1 | 3/2002 | Bergström et al. | 433/173 |
| 6,358,051 B2 | 3/2002 | Lang et al. | 433/173 |
| 6,358,052 B1 | 3/2002 | Lustig et al. | 433/174 |
| 6,382,976 B1 | 5/2002 | Wagner | 433/174 |
| 6,382,977 B1 | 5/2002 | Kumar | 433/214 |
| 6,394,806 B1 | 5/2002 | Kumar | |
| 6,394,809 B2 | 5/2002 | Rogers et al. | 433/174 |
| 6,402,515 B1 | 6/2002 | Palti et al. | 433/174 |
| 6,726,481 B1 | 4/2004 | Zickmann et al. | |
| 7,101,183 B2 | 9/2006 | Augthun et al. | |
| 7,344,376 B2 | 3/2008 | Beaty et al. | |
| 2001/0037154 A1 | 11/2001 | Martin | 623/20.12 |
| 2002/0106610 A1* | 8/2002 | Hurson | 433/173 |
| 2003/0224327 A1 | 12/2003 | Constantino | 433/165 |
| 2004/0038179 A1 | 2/2004 | Kumar et al. | 433/173 |
| 2012/0077151 A1* | 3/2012 | Nary Filho et al. | 433/174 |

\* cited by examiner

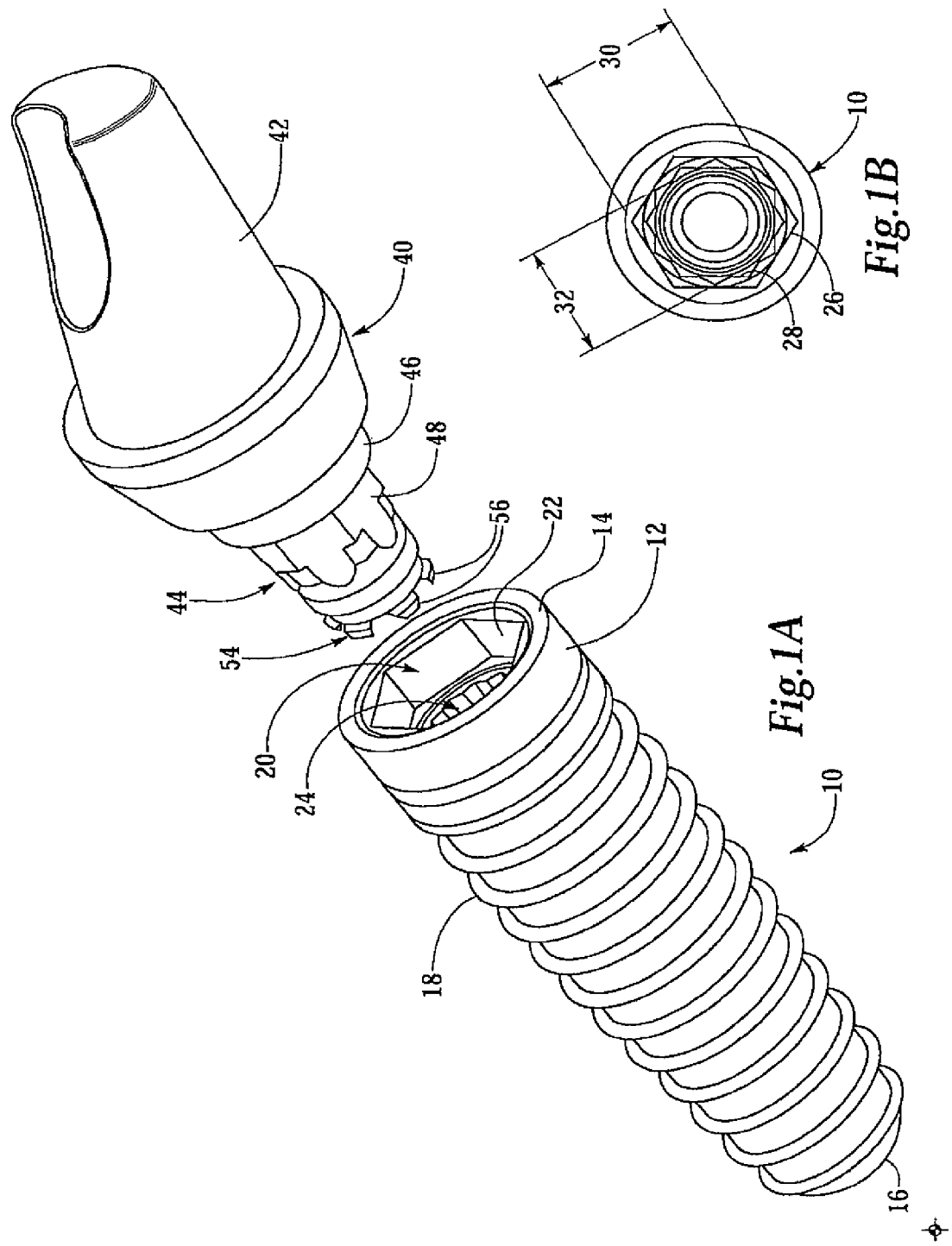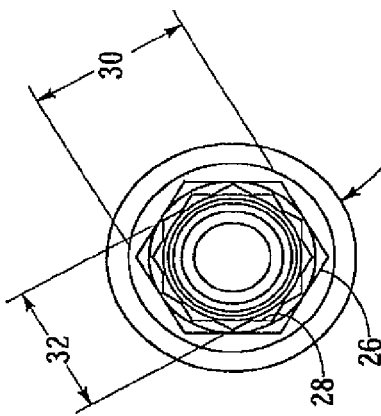

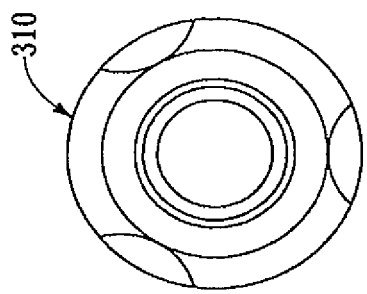
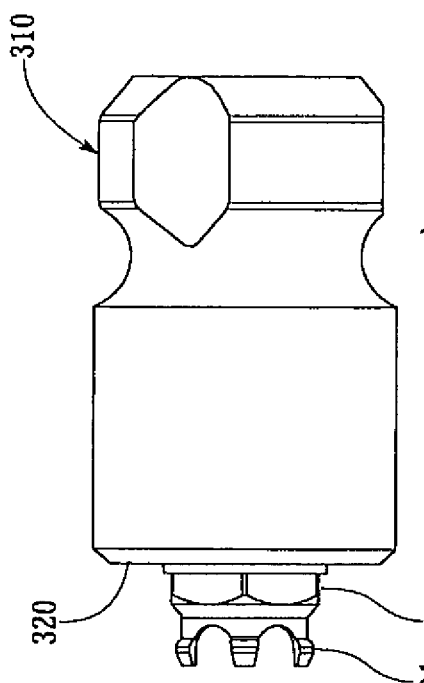
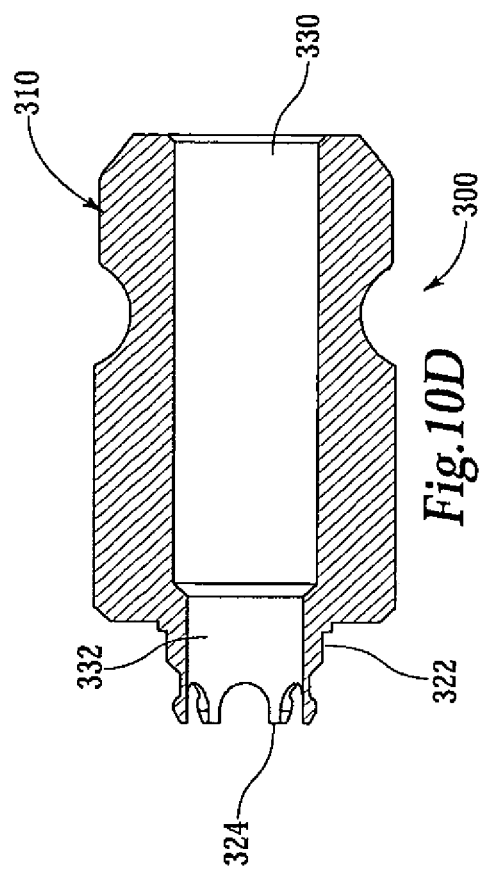
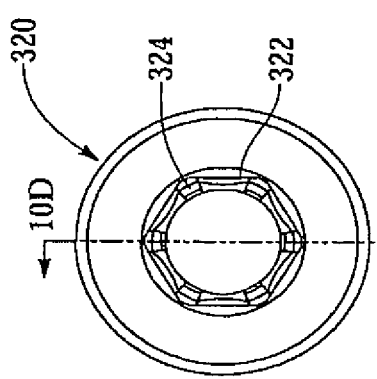

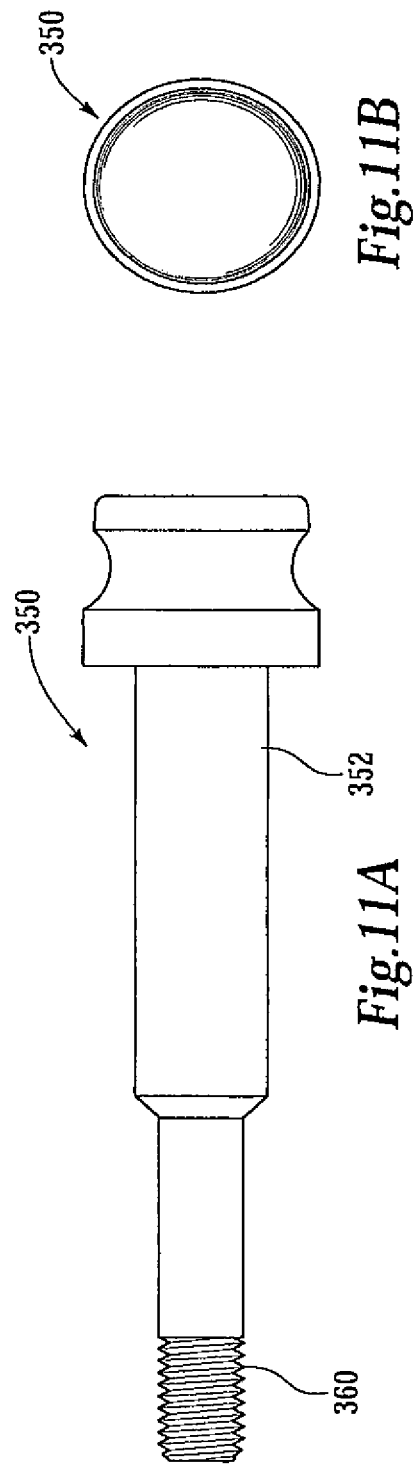
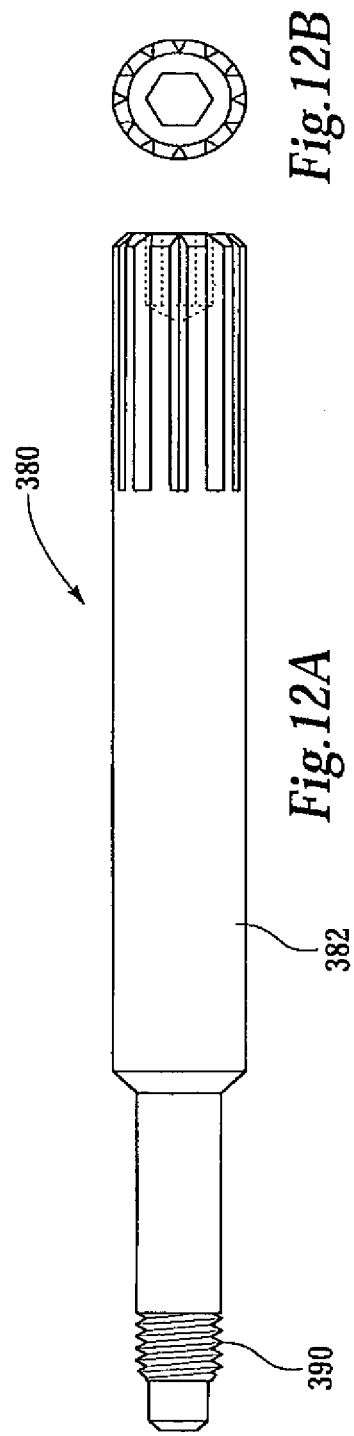

DENTAL IMPLANT SYSTEM

RELATED APPLICATIONS

This application is a division of U.S. patent application Ser. No. 10/713,328, filed Nov. 13, 2003, now allowed, which claims priority of Provisional Application Ser. No. 60/450,541, filed Feb. 26, 2003, and Provisional Application Ser. No. 60/425,976, filed Nov. 13, 2002, all three of which are incorporated by reference in their entirety.

FIELD OF THE INVENTION

This invention relates to dental implants and abutments and related articles.

BACKGROUND OF THE INVENTION

Single tooth restorations present the unique requirement that they must be supported non-rotationally on the underlying abutment. When a prepared natural tooth is the underlying abutment, this requirement is met in the normal course of preparing the abutment with a non-circular cross-section. Likewise, when the underlying abutment is a post fitted onto an implant, this requirement is met by preparing the post with a noncircular cross-section. This latter scenario can be more complicated due to the added connection between the implant and the abutment.

Typically, a dental implant is implanted into the bone of a patient's jaw and comprises a socket, e.g., a bore, which is accessible through the overlying or surrounding gum tissue for receiving and supporting one or more attachments or components which, in turn, are useful to fabricate and support the prosthodontic restoration. Dental implant procedures can use a variety of implanting modalities, for example, blade, threaded implant, or smooth push-in implant. The present invention is not concerned with the implant modality that is used. The invention is, however, concerned with connections between implants and attachments, as well as with other matters.

With respect to connections used in implant systems, internal threads of the implant have been used to connect abutments having threaded stems. Rotational alignment is not, however, easily achieved using threaded connections. Further, such a threaded bore, by itself, cannot generally provide rotational fixing. Rotationally fixing the prosthetic tooth to the abutment, and rotationally fixing the abutment to the implant, must be accomplished to ensure that the prosthetic tooth is non-rotational in the mouth of the patient after the restoration process is complete. To improve the likelihood that the implant will not exhibit movement, the implant is typically allowed to undergo osseointegration prior to being subjected to normal loading.

To overcome the non-rotational deficiency between the implant and attachments, dental implants include an anti-rotational structure to restrain components attached to the implant against rotation relative to the implant around the longitudinal axis through the bore. A common structure used to restrain rotation includes a male projection or a female indentation located on or near the gingival surface of the implant which is concentric with the opening into the bore. These designs are not, however, free of problems.

An inherent disadvantage of implant components is that their small size makes assembly difficult. Problems include the difficulty of properly positioning abutments in implants. The relatively small size of the components and tight working environment make it difficult to know when an abutment is properly seated in an implant. Related problems include abutments becoming loose due to the extreme forces incurred through normal chewing actions. Traditionally, axial retention has been achieved with a screw threading through the abutment and attaching to the implant. More recently, attempts have been made to eliminate the axial screw by using snap-in abutments. These snap-in abutments generally are provided with protrusions extending from the distal end of the stem of the abutment. Some of these snap-in designs are more successful than others. Practitioners have noted that some abutments used in these screwless systems become loose due to the large forces generated through chewing. For some, the disadvantages associated with screwless abutments outweigh any potential benefits.

These screwless abutments also exhibit unacceptable axial movement. This axial movement can lead to damage of the abutment or the implant as a result of misaligned forces and increased internal wear. The internal wear and misaligned forces lead to further unacceptable movement, inevitably requiring repair and replacement. In the mildest cases, the patient is inconvenienced. In the more severe cases, where the patient waits too long, infection and permanent bone and tissue damage occur. Thus, even systems that provide adequate connection must continually be improved upon to reduce patient suffering, or worse.

The prior art has successfully addressed many problems. But not all disadvantages have been overcome, and some solutions carry their own disadvantages.

SUMMARY OF THE INVENTION

This invention, in particular, relates to dental implants and abutments. This invention also relates to rotation-limiting dental connecting mechanisms of the kind employing a non-round projection engaged in a non-round bore to connect two parts endwise in a fashion that limits relative rotation between the parts around their common longitudinal axis. Some embodiments of the present invention are concerned with limiting axial movement between endwise-connected dental implant system parts. This present invention also concerns sensory feedback systems indicative of connection conditions in dental implant systems.

An embodiment of the invention comprises a dental implant having a proximal end adapted to abut an abutment and an interior bore extending distally from the proximal end. As used herein, unless otherwise indicated, a distal location is closer to or deeper in the bone than a proximal location. The implant is provided with a first anti-rotation cavity in the interior bore and a second anti-rotation cavity in the interior bore. The first cavity comprises a first minor diameter and the second cavity comprises a second minor diameter no greater than the first minor diameter of the first cavity. Depending on the application, the second anti-rotation cavity is positioned distal of the first anti-rotation cavity.

The implant may also be provided with an axial retention section distal of the first and second anti-rotation cavities. The axial retention section is adapted to mate with a device inserted into the interior bore. The axial retention section comprises, for some embodiments, a threaded section in the interior bore that is adapted to mate with an abutment screw inserted into the interior bore. In an alternate embodiment, the axial retention section comprises a recess adapted to engage a resilient lip of a device inserted into the interior bore. Another embodiment uses both an abutment screw and a resilient feature to inhibit axial movement.

In another embodiment, the implant is provided with a first feedback feature distal of the first and second anti-rotation cavities. The feedback feature may, for example, comprise male geometry. In yet another embodiment of the implant, the interior bore comprises a feedback feature and an axial retention feature. Anti-rotational features are, in some embodiments, provided in combination with a feedback feature and an axial retention feature.

Another embodiment of the invention is directed toward an implant system. A dental implant system in accordance with the invention comprises an implant, a first abutment, and a second abutment. The implant comprises a proximal end opening to a bore, a first internal anti-rotation cavity in the bore, and a second internal anti-rotation cavity in the bore, wherein the second internal anti-rotation cavity is located distal of the first anti-rotation cavity.

The first abutment comprises a stem adapted to fit in the bore of the implant. The stem comprises a first non-locking portion adapted to be located in the first internal anti-rotation cavity without rotationally-lockingly engaging the first internal rotation cavity. The stem further comprises a locking portion distal of the non-locking portion. The locking portion is adapted to rotationally-lockingly engage the second anti-rotation cavity.

By contrast, the second abutment comprises a stem having a locking portion adapted to rotationally-lockingly engage the first anti-rotation cavity. The stem of the second abutment further comprises a non-locking portion distal of the locking portion. The non-locking portion of the second abutment is adapted to be positioned in the second anti-rotation cavity without rotationally-lockingly engaging the first anti-rotation cavity.

An abutment cross-section need not, however, have the same configuration as that of an implant cross-section for the implant and the abutment to be rotationally locked. For example, a 12-point hexagonal configuration can lock with a 6-point hexagonal configuration. The two cross-sections should, however, be adapted to be engaged such that relative rotation is relatively small and, preferably, substantially eliminated.

The system may comprise one or both of the abutments. Further, in some embodiments, at least one of the abutments is an angled abutment. The angled abutment, in some embodiments, comprises a locking section adapted to interface with at least one of the two or more anti-rotation cavities. Preferably, the abutment is adapted to be rotatable in increments of 30° prior to fixedly engaging it with the implant. That is, the abutment is adapted for 30° indexing. One embodiment of anti-rotational cavity adapted to provide 30° increment rotation comprises a 12-point polygonal socket.

Another system of the invention comprises an implant having a first internal anti-rotation feature and a driving tool adapted to engage the implant through the first internal anti-rotation feature. The system may also comprise an abutment adapted to engage the implant through a second internal anti-rotation feature of the implant.

An alternate implant system of the invention comprises an implant comprising an interior bore and a feedback feature in the interior bore. A threaded section is positioned distal of the feedback feature. The system further comprises an abutment adapted to be attached to the implant.

The abutment comprises a post and a stem extending from the post. The stem is adapted to fit in the interior bore. The stem comprises a complementary feedback feature adapted to cooperate with the implant feedback feature and provide feedback to a practitioner indicating when the abutment is properly seated. The complementary feedback feature may, for example, comprise male geometry. The feedback provided to the practitioner may, for example, comprise tactile or audible output or both tactile and audible output, such as when a resilient member snaps back to its non-deformed shape or position. The feedback system may, alternatively, or in combination with tactile and audible output, provide a visual indication concerning a seating condition of an abutment of coping structure.

An abutment screw is adapted to fit within a through-bore extending through the post and stem of the abutment and retain to the abutment in the implant. The abutment screw comprises a proximal end (e.g., the screw head) adapted to interface with the abutment and a distal end adapted to engage the threaded section of the implant. More generally, the implant may be provided with an internal axial retention section adapted to engage an abutment retention shaft. The axial retention shaft engages an internal axial retention feature of the implant to limit axial movement of the abutment relative to the implant.

Although the invention is directed toward individual components, such as the implant, the abutment, the axial retention shaft, and to systems comprising combinations thereof, other aspects and advantages of the present invention will be apparent to one of ordinary skill in the art from a review of the Applicants' teachings.

BRIEF DESCRIPTION OF THE DRAWINGS

FIGS. 1A and 1B show a perspective view and top view of an implant comprising two internal anti-rotation cavities and an angled abutment positioned for insertion into the implant.

FIGS. 10A-10D illustrate an impression coping transfer cylinder adapted to engage an implant, such as, for example, the implant illustrated in FIGS. 1A and 1B.

FIGS. 11A and 11B illustrate an impression coping transfer screw suitable for use with the impression coping transfer cylinder illustrated in FIGS. 10A-10D.

FIGS. 12A and 12B illustrate a pickup screw suitable for use with the impression coping transfer cylinder illustrated in FIGS. 10A-10D.

DETAILED DESCRIPTION OF THE ILLUSTRATED EMBODIMENT

Figures 2, 3:
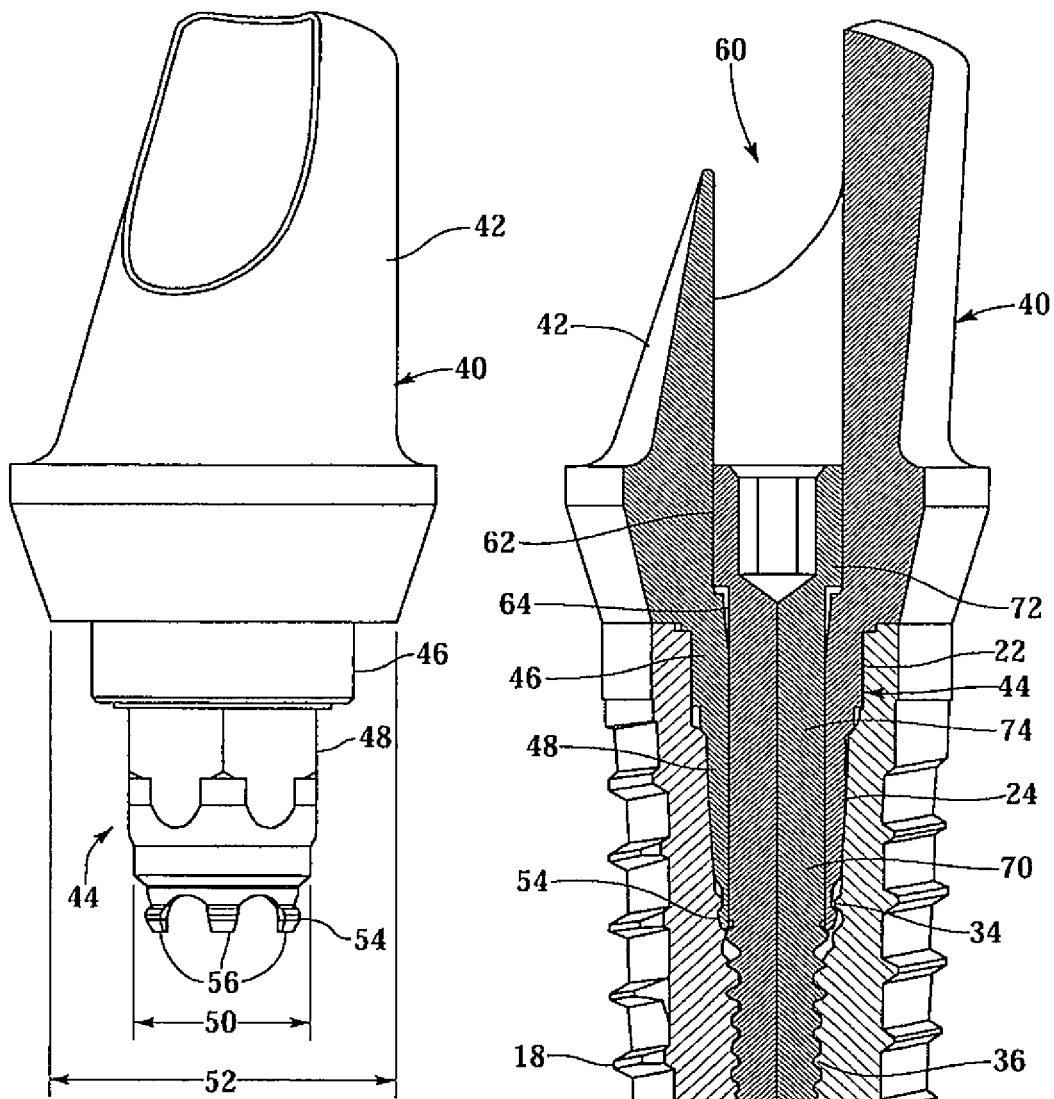
FIG. 2 shows a cut-away sectional view of the implant and abutment shown in FIG. 1, but with the abutment seated in the implant. An abutment screw extends beyond the abutment stem and threadably engages the implant.
FIG. 3 shows a side elevation view of the angled abutment shown in FIGS. 1 and 2 and more clearly illustrates a locking portion and a non-locking portion of a stem of the abutment.

FIGS. 1 and 2 illustrate an implant 10 adapted to be screwed into the bone of a patient and an abutment 40 adapted to be connected to the implant 10. The implant 10 comprises a proximal end 12 including a table 14 adapted to abut the abutment 40. The implant 10 comprises a distal end 16 opposite the proximal end 12 and at least one thread 18 disposed therebetween for screwing the implant 10 into the bone of a patient. An interior bore 20 extends distally from the proximal end 12 toward the distal end 16. The interior bore 20 comprises a first anti-rotation cavity 22 and a second anti-rotation cavity 24 distal of the first anti-rotation cavity 22.

In FIG. 1, the two cavities 22 and 24 are separate, distinct and slightly spaced apart, and are connected with a tapered section. Other arrangements, however, are equally suitable, such as, for example, where the cavities are adjacent and step-wise connected, or spaced apart and connected by one or more cavities.

Focusing on FIG. 1B, an end view of the implant 10 is shown. In the embodiment illustrated in FIG. 1B, the first anti-rotation cavity of implant 10 comprises a hexagonal socket 26. The hexagonal socket 26 comprises a plurality of obtuse interior angles. By contrast, the second anti-rotation cavity 24 comprises a 12-point polygonal socket 28 including a plurality of obtuse interior angles. The hexagonal socket 26 comprises a minor diameter 30 and the 12-point polygonal socket 28 comprises a minor diameter 32. The minor diameter 32 is less than the minor diameter 30 of the hexagonal socket 26. And, the major diameter of the hexagonal socket 26 is larger than the minor diameter 32 of the 12-point polygonal socket 28. In one embodiment, the minor diameter 30 is approximately 0.11 inch and the minor diameter 32 is approximately 0.09 inch. For some embodiments, the difference between the major and minor diameters is in the range of 0.0005 and 0.1 inch. As used herein, the term minor diameter refers to the diameter of the largest cylinder sized to fit within a polygonal cavity, whereas the term major diameter is the diameter of a cylinder contacting the external points at corners of such a cavity.

For some applications, at least one of the anti-rotation cavities 22 and 24 is adapted to mate with a conventional driving tool, for example, a tool with a working end comprising a square, a pentagon, a hexagon, an octagon, etc. Preferably, at least the other cavity is adapted to mate with an abutment stem having a predetermined shape. Some tools are described in FIG. 9.

In one conventional implant system, an implant comprises an external hexagon, i.e., a hexagonal projection, for engaging a driving tool. The driving tool applies relatively significant amounts of torque to the external hexagonal projection to screw the implant into the patient's bone. After the implant is screwed into place and healing has occurred, an abutment is mated with the external hexagonal projection and seated on the implant. Unfortunately, the significant amount of torque applied to the hexagonal projection often mars and distorts the hexagonal configuration. This distortion can, in some applications, result in play, or wiggle-room, between the implant and the abutment.

To overcome this distortion-related problem, the implant 10 has been provided with the first and second anti-rotation cavities 22 and 24. The implant 10 may, for example, be driven with a driving tool through the first anti-rotation cavity 22. The abutment 40 can then be mated with the second anti-rotation cavity 24, which has not been subjected to driving torques as was the first anti-rotation cavity 22. The second anti-rotation cavity 24 is in pristine condition, enabling a tight fit to occur between the abutment 40 and the implant 10. Although the invention is not limited to internal anti-rotational features, an advantage of internal anti-rotation cavities, over external projections, is that the cavity can generally be longer (deeper) than would be possible with an external feature. The longer length provides greater surface area for engaging a driving tool. Thus, there is a smaller chance of damaging the implant during installation.

The cavities illustrated in FIG. 1B are generally straight and comprise perimeters generally parallel with a longitudinal axis. Other shapes, such as frusto-conical, are appropriate for different applications. For such shapes, analogues of the terms major and minor diameter are applicable.

Turning to FIG. 2, which illustrates a partial sectional view, the abutment 40 is shown abutting, i.e., seated on, the implant 10. The interior bore 20 of the implant 10 comprises a feedback feature 34 for interfacing with the abutment 40 and providing feedback to a practitioner indicating when the abutment 40 is properly seated within the implant. The feedback feature 34 may, for example, comprise male geometry. Distal of the implant feedback feature 34 is an axial retention feature 36 embodied in the form of a plurality of threads. An abutment screw 70 extends through the abutment 40 and interfaces with the threads of the axial retention feature 36 to limit axial movement of the abutment.

Referring to FIGS. 1 and 2, the abutment 40 comprises a post 42 and a stem 44 extending in a relative downward direction from the post 42. The stem 44 comprises a non-locking portion 46 adapted to be positioned in the first anti-rotation cavity 22 when the abutment 40 is seated in the implant 10. The stem 44 further comprises a locking portion 48 adapted to be positioned in the second anti-rotation cavity 24 when the abutment 40 is positioned in the implant 10. The locking portion 48 is adapted to rotationally-lockingly engage the second anti-rotation cavity 24, wherein the abutment 40 is prevented from rotating relative to the implant 10.

For some applications, it is desirable to be able to increment the angled abutment 40 in steps to achieve the proper functional and cosmetic alignment of a prosthetic ultimately affixed to the post 42, i.e., the abutment may be indexed. Accordingly, the locking portion 48 and the second anti-rotation cavity 24 are adapted to provide a predetermined minimum rotational increment. The illustrated embodiment has a minimum rotational increment of 30° due to the 12-point shape. Once the abutment 40 is rotationally aligned, the practitioner can apply pressure to seat the abutment 40, while being sensitive to feedback indicative of the abutment's seating status.

The polygonal shape is not required to have actual points. Other forms of interface, for example, indentations and projections, are suitable to limit rotation between the implant 10 and the abutment 40. Furthermore, shapes other than polygons are suitable for limiting rotation between the components. The actual rotational increment size will depend, at least in part, on the anti-rotation feature in the second cavity 24 and the shape of the locking portion 48.

Turning briefly to FIG. 3, to rotationally lock the locking portion 48 to the implant 10, the locking portion 48 comprises a major diameter 50 greater than the minor diameter 32 of the second anti-rotation cavity 24. The major diameter 50 is greater than the minor diameter 32 so the projections and indentations engage to limit, or eliminate, rotation between the implant 10 and the abutment 40. In contrast, the non-locking portion 46 comprises a major diameter 52 smaller than or approximately equal to the minor diameter 30 of the first anti-rotation cavity 22. Thus, the non-locking portion 46 of the abutment 40 does not rotationally engage the implant 10.

Returning to FIG. 2, the abutment 40 comprises a feedback feature 54 adapted to engage the implant 10 as the abutment 40 is being seated and to provide an indication to the practitioner when the abutment 40 is properly seated. The feedback features 34 (of the implant 10) and 54 (of the abutment 40) may collectively comprise one or more resilient members adapted to deform during the seating process and reform when the abutment is properly seated. With reference to FIGS. 1 and 3, the feedback feature 54 of the abutment 40 comprises a plurality of resilient fingers 56 located at the distal end of the stem 44.

The feedback system may be a system adapted to provide only tactile feedback, or only audible feedback or both tactile and audible feedback. A system is considered to provide feedback when the sensory output is of a sufficient level so as to be sensed by a practitioner without the practitioner taking extraordinary steps to receive the feedback. Generally, use of tactile feedback and audible feedback, alone or in combination, is desirable in many applications due to the relative simplicity of such systems and the advantages of such systems over current verification practices.

Verification techniques involve additional steps, typically taken immediately after the practitioner performs the abutment-seating steps, that often use additional equipment. Current verification practices typically involve the use of radiographic equipment, e.g., an X-ray. Use of radiographic equipment is both relatively costly and time-consuming. The practitioner must adjust the equipment to take a proper image, and typically step out of the room to snap the image. The patient is also exposed to another dose of radiation. Such verification systems are both costly and time-consuming. In contrast, a feedback system does not have the attendant costs and delays of verification systems. The feedback system of the present invention operates, in a practical sense, contemporaneous with the seating process. A verification process involves identifiable steps separate from those required to seat an abutment.

In some embodiments, the abutment 40 is adapted to be axially-restrained in the bore 20 without additional components. In essence, the abutment 40 is autonomously axially-restrained when seated. The stem 44 of the abutment 40 comprises axial retention features adapted to interface with axial retention features in the abutment interior bore 20. In the illustrated embodiment, the implant feedback feature 34 and the abutment feature 54 also have retention capability. The axial retention feature 54 comprises the plurality of fingers 56 that are adapted to provide both feedback and retention capabilities.

Other structures are suitable for providing one or both axial retention and feedback capabilities. In some embodiments, including some comprising resilient members providing both retention and feedback, an additional axial retention structure is required, or at least desirable. Such additional axial retention structure may be integral with one or both of the abutment 40 and the implant 10. Alternatively, the structure may be separate, but coupled to and relatively fixed, with respect to one of either the abutment or the implant. Furthermore, separate additional axial retention structures need not be relatively fixed to either one of the abutment or the implant. For example, the separate additional retention structure may also be provided as an abutment retention shaft that interfaces with one or both the abutment 40 and the implant 10, yet is separable from both. One example of an abutment retention shaft is the abutment screw 70 illustrated in FIG. 2.

In FIG. 2, a through-bore 60 extends through the post 42 and the stem 44 to allow the abutment screw 70 to be inserted therein. The through-bore 60 comprises a first diameter 62 and a second diameter 64 distal of the first diameter 62 and smaller than the first diameter 62. The abutment screw 70 is inserted into the through-bore 60 to threadably engage the threads 36 of the implant 10.

In FIG. 2, the abutment screw 70 comprises a screw head 72 adapted to couple with a driving tool, for example, an Allen wrench. Other abutment screw head driving structure, e.g., a square driver, a flat head screwdriver, a Phillips screwdriver, will be suitable. A shank 74 extends distally from the head 72 to a distal threaded end 76. The head 72 comprises a first diameter, and the shank 74 comprises a second diameter smaller than the head diameter. The head diameter is preferably larger than the through-bore 60 second diameter 64 to prevent the abutment from moving axially past the screw head 72. Thus, after the abutment screw 70 threadably engages the implant 10, the screw 70 acts to retain the abutment 40 in the implant 10.

Figures 4A, 4B:
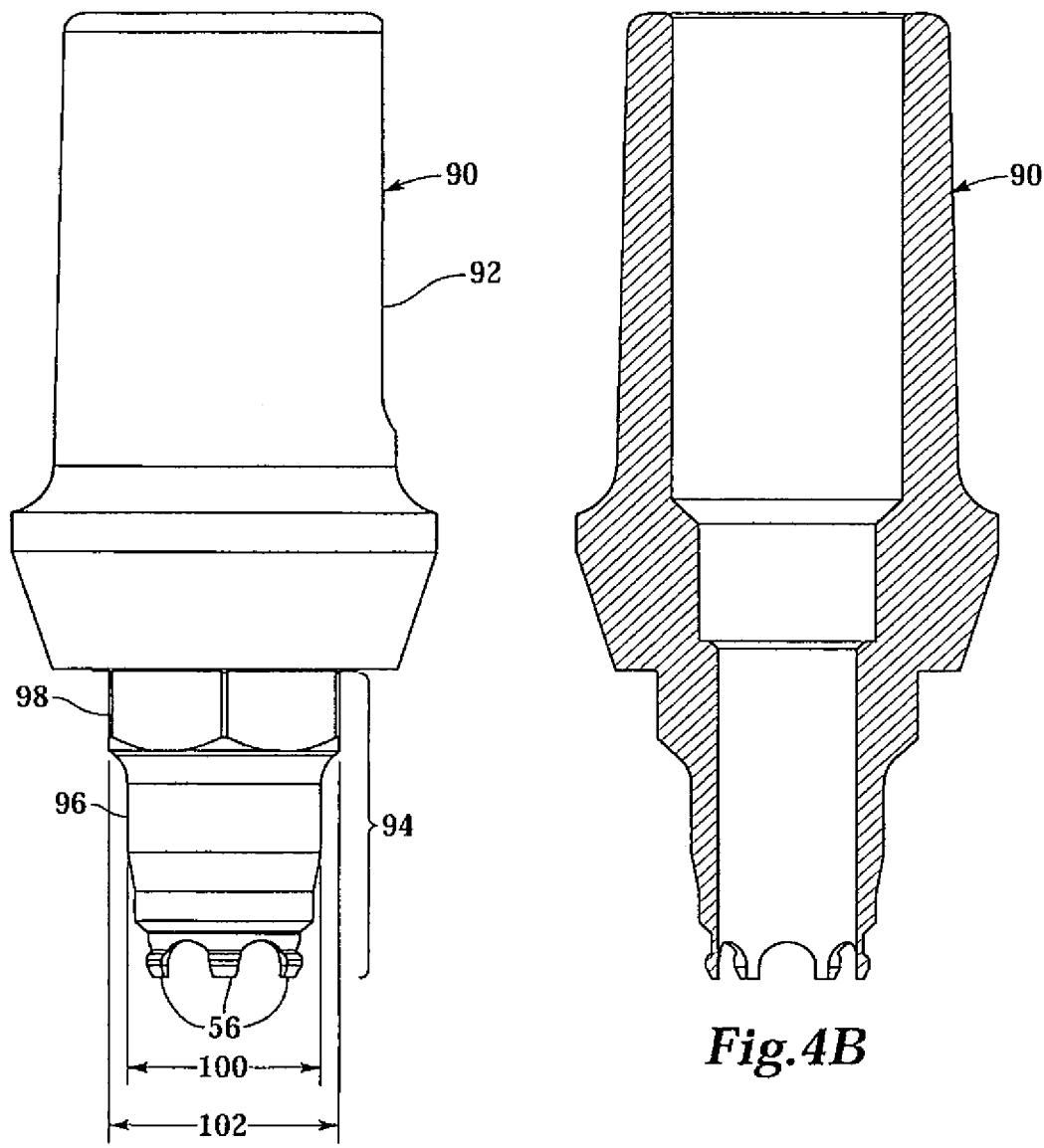
FIGS. 4A and 4B show side elevation and cross-sectional views of a straight abutment comprising a stem having a locking portion and a non-locking portion, where the portions are in reverse order as compared to those of the angled abutment shown in FIG. 3.

The system may also comprise a straight abutment 90, for example, illustrated in FIG. 4, which is compatible with the implant 10. The straight abutment 90 comprises a post 92 and a stem 94. The stem 94 comprises a non-locking portion 96 and a locking portion 98. In contrast to the angled abutment 40, the non-locking portion 96 is distal of the locking portion 98.

Figure 5:
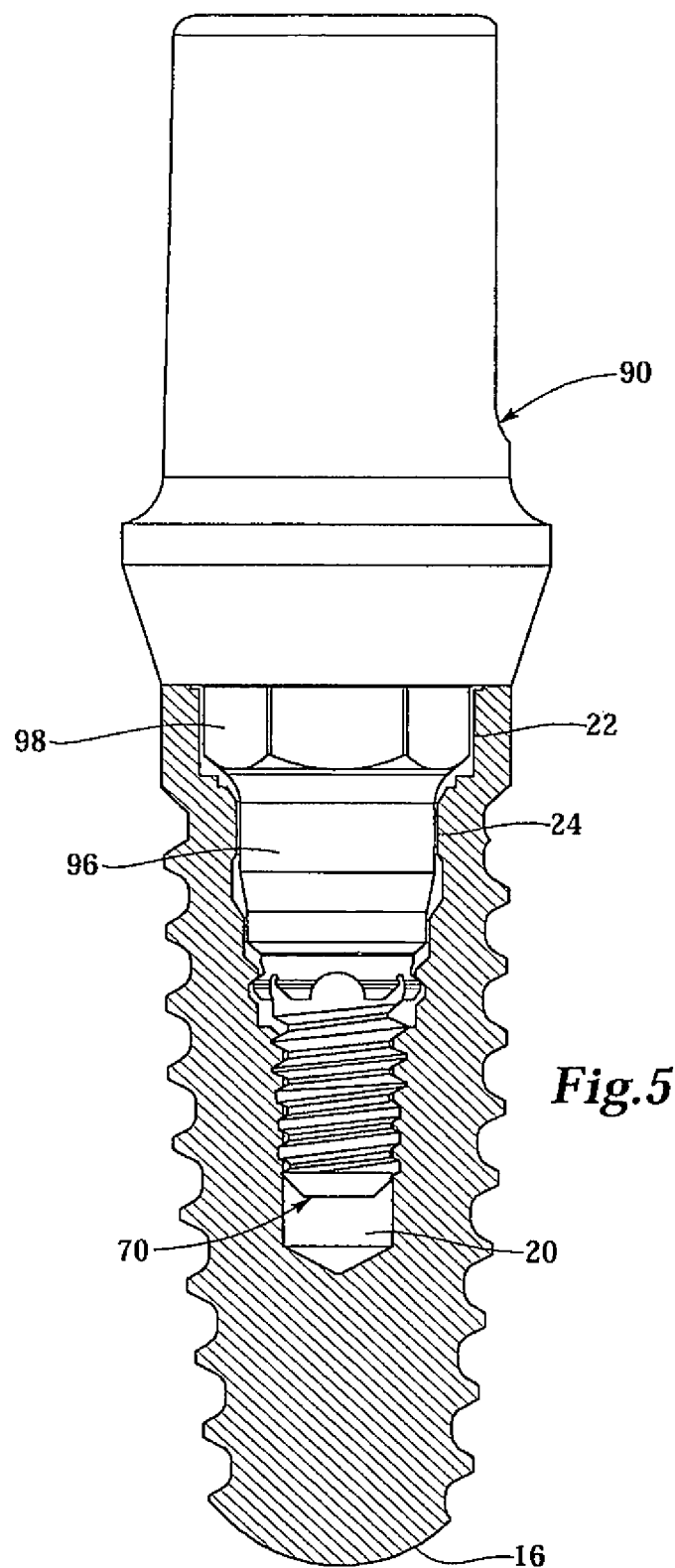
FIG. 5 shows a partial side elevation view with part of the implant cut away to show the straight abutment illustrated in FIG. 4 seated in the implant and axially secured with an abutment screw.

FIG. 5 is a side elevation view showing the straight abutment 90 seated in the implant 10. Part of the implant 10 is cut away to better illustrate the straight abutment 90 and part of the abutment screw 70, which acts to limit axial movement of the abutment. The locking portion 98 is adapted to rotationally-lockingly engage the first anti-rotation cavity 22 when the abutment 90 is positioned in the implant 10. The non-locking portion 96 does not so engage the second anti-rotation cavity 24.

To avoid rotational lock between the implant 10 and the second cavity 24, the non-locking portion 96 has a major diameter 100 (FIG. 4) no larger than the minor diameter 32 of the second anti-rotation cavity 24. To provide rotational engagement between the stem 94 and the implant 10, the locking portion 98 has a major diameter 102 (FIG. 4) that is larger than the minimum diameter 30 of the first anti-rotation cavity 22. Thus, in embodiments illustrated in FIGS. 1-5, the angled abutment 40 rotationally engages the implant 10 through the second anti-rotation cavity 24, whereas the straight abutment 90 rotationally engages the implant 10 through the first anti-rotation cavity 22.

The first anti-rotation cavity 22 may comprise a configuration including interior acute angles while the second anti-rotation cavity 24 comprises a configuration including interior obtuse angles. Furthermore, both cavities may be provided with the same type of configuration, but of differing diameters. Additionally, the straight abutment 90 may be adapted to engage the implant 10 through the second anti-rotation cavity 24, whereas the angled abutment 90 is adapted to engage the implant 10 through the first anti-rotation cavity 22.

To facilitate compatibility among components, a system in accordance with principles of the invention may comprise an implant having one internal anti-rotation feature for engaging both straight and angled abutments and another internal anti-rotation feature for engaging a driving tool. The one internal anti-rotation feature may be adapted to engage the driving tool as well as the abutments. Similarly, the other anti-rotation feature may be adapted to engage multiple abutment stem types as well as the driving tool. And although the invention is primarily described with respect to implants having two internal features, principles of the invention are not so limited. An implant may be provided with a single internal anti-rotation feature, with a single external anti-rotation feature, with two or more internal features, or two or more external features, or various combinations.

Figure 6B:
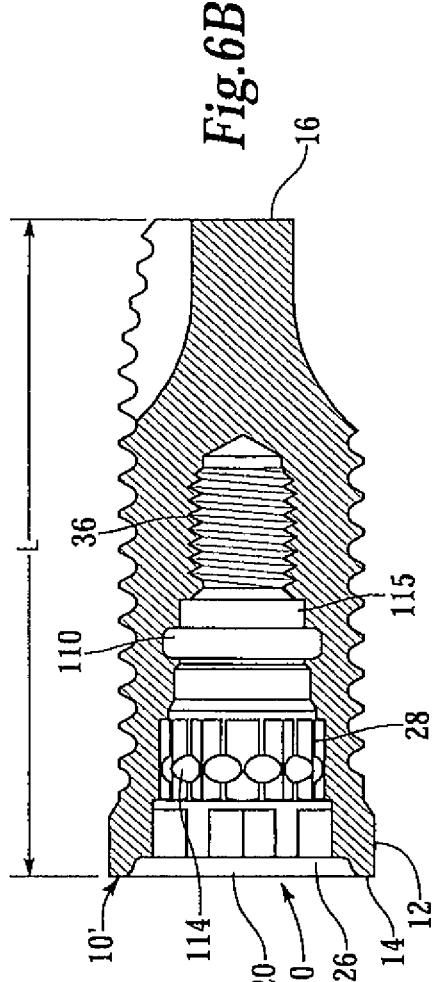
FIGS. 6A-6E illustrate an alternative embodiment of an implant.
Figure 6A:
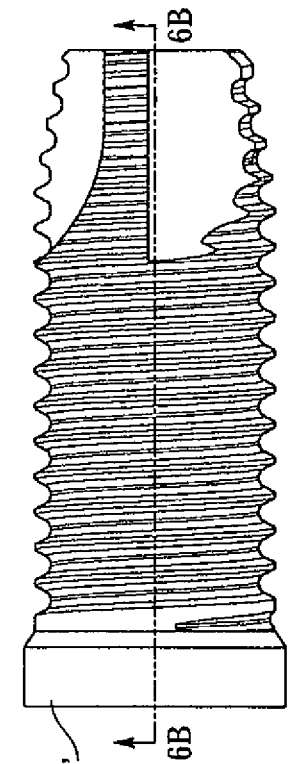
Figure 6D:
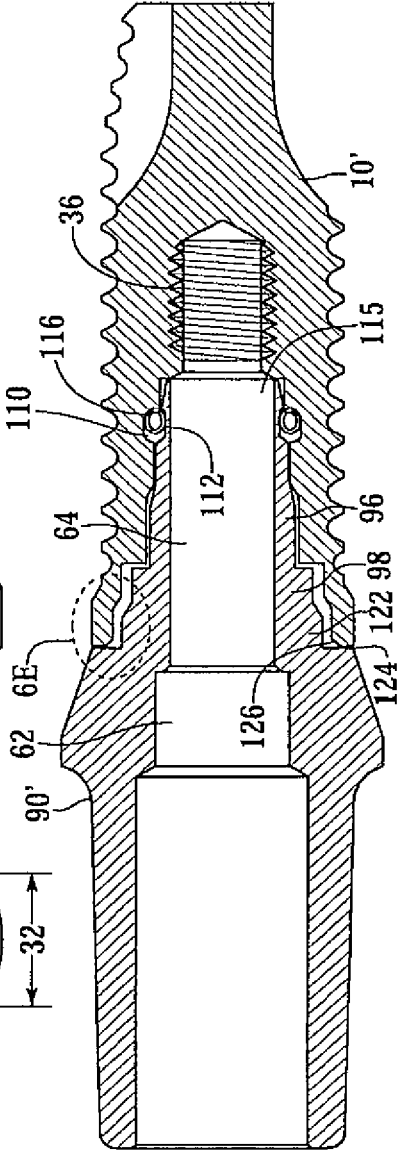
Figure 6C:
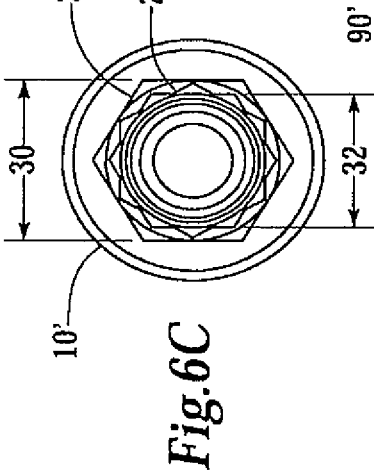

FIG. 6A illustrates a side view of an implant 10'. FIG. 6B is a section view taken along such line 6B-6B of the implant 10' in FIG. 6A. FIG. 6C is an end view looking down the bore of the implant 10'. The implant 10' is generally similar to the implant 10, except that the interior bore 20 of the implant 10' comprises a recess 110 adapted to retain a toroidal flexible member, such as a toroidal spring, that may interface with an abutment as the abutment is seated. The toroidal flexible member provides feedback to the practitioner indicating when the abutment is properly seated. The toroidal flexible member may, for example, comprise male geometry, for example, a round tube formed into a toroid. FIG. 6D illustrates a straight abutment 90' seated in the implant 10'.

Figure 6E:
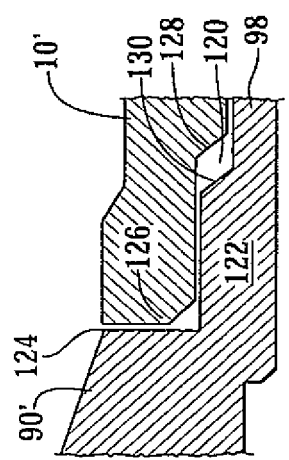
Figure 7A:
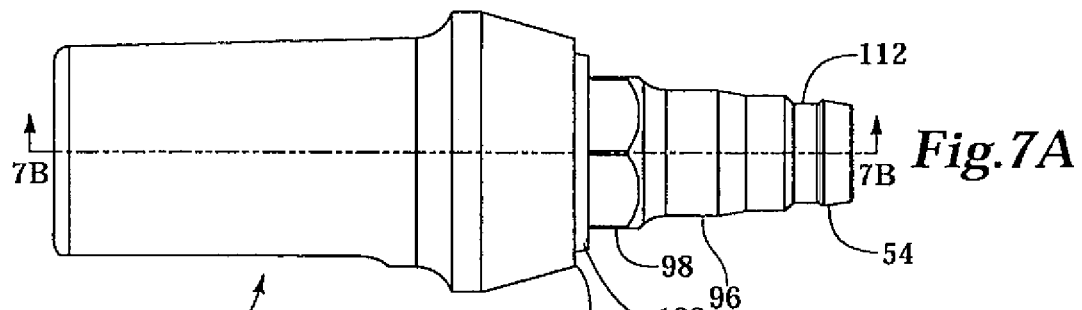
FIGS. 7A and 7B illustrate an alternative embodiment of a straight abutment adapted to mate with the implant illustrated in FIGS. 6A-6E.
Figure 7B:
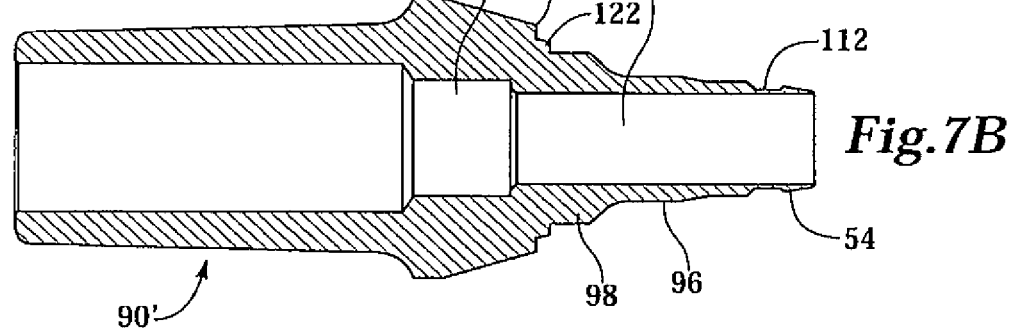
Figure 8A:
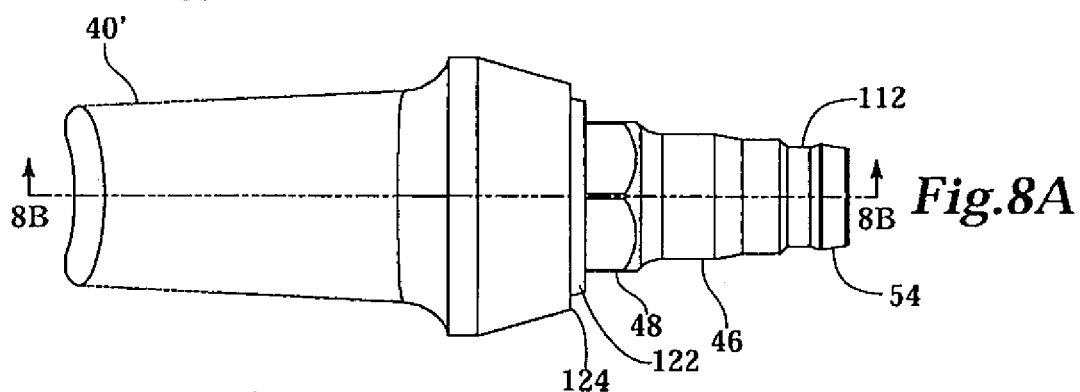
FIGS. 8A and 8B illustrate an alternative angled abutment adapted to mate with the implant illustrated in FIGS. 6A-6E.
Figure 8B:
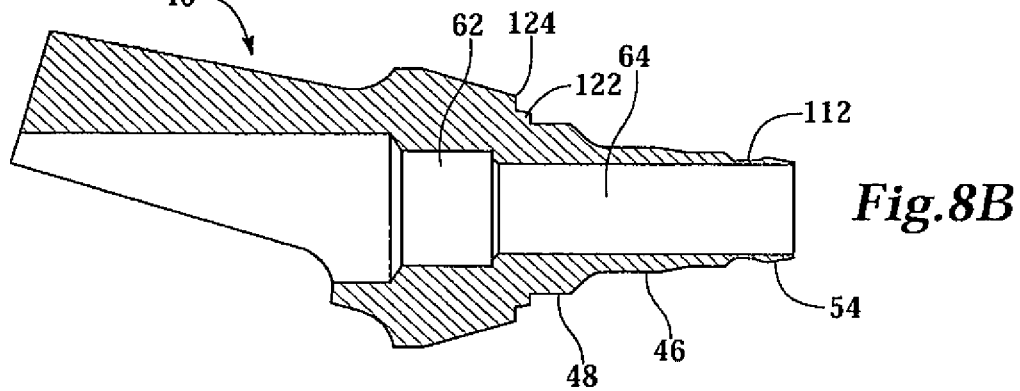

FIGS. 7 and 8 illustrate abutments adapted to interface with the implant 10' shown in FIG. 6. FIG. 7A is a side elevation view of a straight abutment 90'. FIG. 7B is a section view along section line 7B-7B of FIG. 7A. FIG. 8A is a side elevation view of an angled abutment 40'. FIG. 5B is a section view along section line 8B-8B of FIG. 5A. The stems of both the straight abutment 90' and the angled abutment 40' comprise a complementary recess 112. The recess 112 is positioned to be adjacent the recess 110 in the interior bore 20 of the implant 10' when the abutment is seated. The recess 110 and the complementary recess 112 define an area in which a toroidal ring would rest when the abutment is seated.

With reference to FIGS. 6B and 6D, the implant 10' includes a second groove 114 for providing feedback. The second groove 114 is also useful in the implant 10 of FIGS. 1-5. The second groove 114 is useful for retaining a driving tool or other component, for example, an impression coping, in operable contact with the implant 10'. In one embodiment of the embodiment illustrated in FIG. 6, the implant 10' has a length L that, for some applications, is approximately between 0.3 inch and 0.9 inch. The first and second anti-rotation cavities 26 and 28 extend into the bore a combined depth of approximately 0.1 to 0.2 inch. A finger passage 115 extends to a depth of approximately 0.1 to 0.3 inch. The second groove 114 has a mid-line positioned approximately 0.01 to 0.2 inch from the table 14. The recess 110, beginning at a depth of approximately 0.1 to 0.3 inch, has a width of approximately 0.01 to 0.2 inch. These dimensions are illustrative and suitable for particular applications, but are not the only suitable dimensions for a dental implant in accordance with the Applicants' teachings. A toroidal spring 116 is positioned in the area defined by the recess 110 and the complementary recess 112. The toroidal spring 116 acts against the resilient member 54 to apply a retention force to the straight abutment 90'.

With reference to FIGS. 6B, 6D, 6E, 7A and 7B, to reduce stress, the implant 10' comprises a counterbore 120 to receive a base 122 of the abutment 90'. In FIG. 6E, part of the abutment 90' is removed to aid illustration. The base 122 is positioned between a margin 124 and the locking portion 98 that mates with the first anti-rotation cavity 26. Counterbore 120 has a diameter of approximately 0.10 to 0.15 inch and a depth of approximately 0.01 inch. To reduce point stresses, the counterbore 120 comprises a chamfer 126 and a fillet 128 with dimensions approximately 0.001 to 0.01 inch. The base 122 comprises a chamfer 130 corresponding to the fillet 128. The chamfers 130 and 126 together facilitate placing the abutment 90' into the implant 10'.

Figures 9A, 9B, 9C:
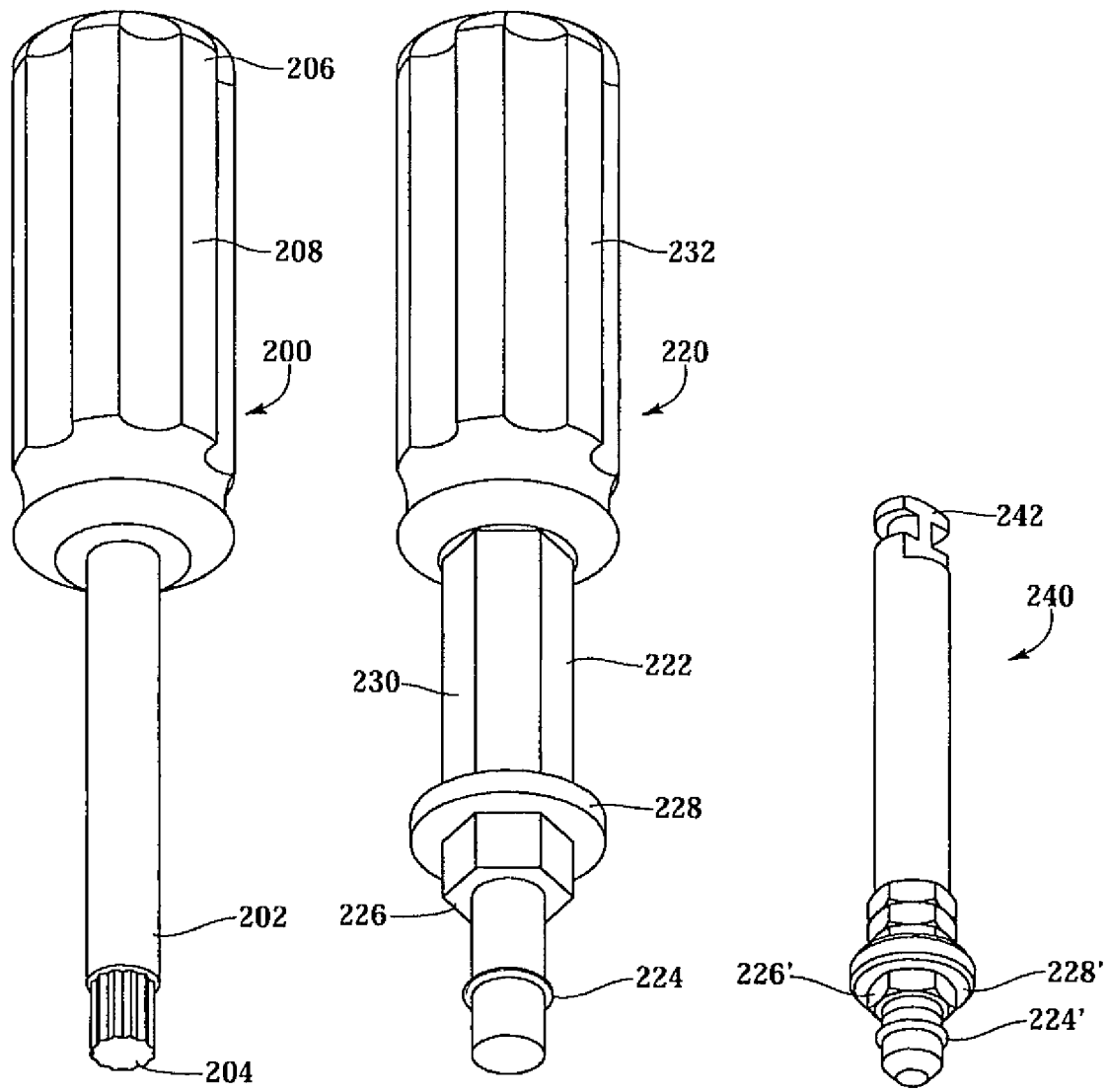
FIGS. 9A-9C illustrate driving tools for driving the implant into the bone of the patient.

FIG. 9A is a perspective view of one type of a driving tool 200 adapted to mate with the second anti-rotation cavity 28 of the implant 10' or the implant 10. The driving tool 200 comprises a first end 202 comprising a 12-point polygonal male geometry 204 adapted to mate with the second anti-rotation cavity 28. An opposing end 206 comprises a handle 208 to facilitate gripping the driving tool 200.

FIG. 9B illustrates another type of driving tool 220 adapted to mate with the first anti-rotation cavity 26 of the implant 10' or the implant 10. The driving tool 220 comprises a first end 222, on a working end, that is adapted to fit within the bore 20 of the implant 10'. The first end comprises a resilient ring, such as an O-ring 224, that couples with the second recess 114 of the implant 10' to help retain the driving tool 220 in proper engagement with the implant 10'. The working end 222 of the driving tool 220 comprises a hexagonal male geometry driving portion 226 adapted to mate with the anti-rotation cavity 26. The diameter distal of the O-ring 224 is sized to fit within the second anti-rotation cavity 28. The working end 222 includes a stop 228 that abuts against the table 14 of the implant 10' when the driving tool 220 is properly seated. The O-ring 224 and the stop 228 cooperate to reduce, and preferably eliminate, unwanted axially motion of the drive tool 220 relative to the implant 10'. The O-ring 224 may be adapted to provide tactile or audible, or both tactile and audible, feedback indicative of a seating condition of the driving tool. The stop 228 provides at least a visual feedback.

An alignment portion 230 of the working end 222 comprises a hexagonal shape aligned with the hexagonal driving portion 226. The alignment portion 230 facilitates aligning the driving portion 226 with the first anti-rotation cavity 26 while the driving tool 220 is being coupled with the implant 10'. After the tool 220 is mated with the implant 10', the alignment portion 230 provides a visual indication as to how the implant 10' anti-rotation cavity 26 is aligned in the mouth of the patient, e.g., the rotational alignment of the implant 10'. The illustrated alignment portion 226 comprises male alignment geometry in the form of the hexagonal shape. Alternative to, or in combination with, the male alignment geometry, the working end 230 may be provided with visual alignment indicia, such as lines running along the length of the working end 230.

The driving tool 220 may be provided with a handle 232 to facilitate gripping the driving tool 220. The handle 232 is not required, however, as the alignment portion 230 may comprise sufficient structure to aid gripping the driving tool 220.

FIG. 9C illustrates a driving tool 240 that is similar to the driving tool 220 illustrated in FIG. 9B. The driving tool 240 comprises a hexagonal driving portion 226' and a stop 228' and an interface structure 224' that facilitates interfacing the driving tool 240 with the bore of an implant. And, the driving tool 240 comprises an iso-latch 242 that is to couple the driving tool 240 to a power driving mechanism.

FIG. 10A illustrates a side elevation view of a transfer impression coping cylinder 300. The impression coping comprises an impression end 310 for interfacing with impression material and an implant interface end 320 for interfacing with an implant. The implant interface end 320 comprises an anti-rotation section 322, e.g., a hexagonal extension, and a resilient interface 324 to temporarily hold the transfer cylinder 300 in an implant until a screw secures the cylinder to the implant. FIG. 10B illustrates an end view of the transfer cylinder 300 showing the implant interface end 320. FIG. 10C illustrates an end view of the impression end 310. FIG. 10D illustrates a section view taken along section line 10D-10D of FIG. 10B. The cylinder 300 includes a through-bore 330 with a reduced cross-section portion 332.

FIG. 11A illustrates an impression coping transfer screw 350 suitable for use with the transfer cylinder 300. The transfer screw 350 comprises a shaft 352 that is sized to extend through the through-bore 330 of the transfer cylinder 330 and connect to the implant via threads 360. FIG. 11B is an end view of the transfer screw 350.

FIG. 12A illustrates a twist lock pickup impression screw 380 suitable for use with the transfer cylinder 300. The transfer screw 380 comprises a shaft 382 that is sized to extend through the through-bore 330 of the transfer cylinder 330 and connect to the implant via threads 390. FIG. 12B is an end view of the transfer screw 380.

The impression coping components illustrated in FIGS. 10-12 are described in further detail in U.S. Pat. No. 5,685,715, which is incorporated herein by reference in its entirety. Such an impression coping can be prepackaged and delivered to the clinician with the implant such that the coping serves as a mount that receives torque for installing the implant into the bone of the patient. Consequently, the present invention contemplates using one of the anti-rotational features of the implant for engaging the mount, rather than, for example, one of the driving tools shown in FIG. 9, and another anti-rotational feature for engaging an abutment or coping if the coping is not used as a mount.

One method for improving connectivity in accordance with the invention includes coupling an abutment to an implant positioned in a patient, and sensing a tactile feedback associated with seating the abutment. Subsequent to sensing the tactile feedback, the implant is engaged with retention structure to resist axial movement of the abutment relative to the implant. The retention structure may be rotated while engaging a thread and allowed to move deeper into the implant as the retention structure is rotated.

The retention structure may be engaged with the implant to limit axial movement of the abutment relative to the implant, but allow some movement of the abutment when a dislodging force is applied to the abutment. For example, the retention structure may threadably engage the implant, but prior to fully screwing the structure down, the abutment can be unseated if a sufficient force is applied. In this manner, a practitioner, e.g., a dentist, can apply a test force insufficient to dislodge the abutment but sufficient to verify that the abutment has not become loose. This avoids problems associated with applying forces, through the retention structure, to an abutment that has become misaligned subsequent to having been seated.

To reduce unwanted rotation between an implant and an abutment, a torque is applied to a first internal anti-rotation feature of the implant to insert the implant deeper into a bone. Subsequent to applying the torque to the first internal anti-rotation feature, an abutment is engaged with a second internal anti-rotation feature of the implant. Such a process allows the abutment to engage a pristine feature, one not damaged while inserting the implant into the patient.

Another advantage of using an implant that has two internal anti-rotation features is that a suitable abutment can be selected from a plurality of abutments and the selection can be based, at least in part, upon prevailing conditions in the patient's mouth. Generally, this use of an implant having two or more anti-rotation features results in a wider assortment of abutments that can be mated to the implant than can be mated to an implant comprising only one anti-rotation feature. While each abutment type is theoretically available with any stem type, a suitable abutment is not as readily available as a practitioner would like. A suitable abutment has a stem that, in fact, can be mated to the osseointegrated implant and is suitable for other prevailing conditions in the patient's mouth. To reduce problems associated with not having a suitable abutment, a practitioner installs an implant comprising two internal anti-rotation features. The practitioner can then be fairly confident that when it comes time to attaching an abutment, a suitable abutment having a stem adapted to engage at least one of the features will be available.

The invention clearly reduces connectivity problems and other problems encountered in the field of dental implants. Applying principles of the invention to dental restoration processes yields improved results. The likelihood of a suitable abutment being available, when needed, is increased, while reducing the amount of planning required. And, costs may also be reduced by eliminating or reducing the need to use verification equipment, such as radio-graphic equipment, during the restoration process.

Use of terms such as first, second, up, below, etc., are for convenience in describing the illustrated embodiments and such use is not intended to limit the variety of embodiments of the invention. Similar features are identified throughout with similar numbers to aid understanding but not to indicate such features are required to be identical among the various embodiments.

The foregoing description of the invention is illustrative and explanatory. Various modifications and alterations to the embodiments disclosed herein will be apparent to those skilled in the art in view of this disclosure. It is intended that all such variations and modifications fall within the spirit and scope of this invention as claimed.

What is claimed is:

1. A dental implant system, comprising:
a screw including a head and a threaded end portion;
a dental implant comprising:
  a proximal end;
  an internal bore extending distally from the proximal end, the internal bore including an upper tapered section, an anti-rotation section having a non-round shape and including at least one planar surface, a lower section having a dimension that is smaller than a dimension of the anti-rotation section, and a threaded section distal of the lower section, the anti-rotation section being located between the upper tapered section and the lower section;
  an external surface including an external-threaded section, a portion of the anti-rotation section being located distal to a proximal end of the external-threaded section of the implant; and
a unitary abutment for attachment to the dental implant comprising:
  a tapered first section including a first dimension and being received in the upper tapered section of the internal bore of the implant;
  a second section having a predetermined shape adapted to rotationally lock with the anti-rotation section of the dental implant, the second section including a second dimension that is smaller than the first dimension of the tapered first section;
  a third section including a third dimension that is smaller than the second dimension and adapted to assist axial insertion of the abutment into the dental implant, the second section being located between the first section and the third section, the third section of the abutment having a cylindrical shape;
  a tapering section that is above the first section and outside of the implant, the tapering section tapering outwardly in a direction from the implant toward a proximal end of the abutment;
  a prosthesis-supporting section that is above the tapering section and configured to support a prosthesis, the prosthesis-supporting section having a length that is greater than a length of the tapering section;

a through-bore extending along a longitudinal axis of the abutment; and an internal shoulder integrally formed within the abutment and partially defining the through-bore, the internal shoulder engaging the head of the screw when the screw passes through the through-bore and the threaded end portion threadably engaging the threaded section of the internal bore of the dental implant so as to axially retain the abutment on the implant with the tapered first section of the abutment received in the upper tapered section of the internal bore of the implant, the axial retention inhibiting axial movement of the abutment distally and proximally relative to the implant.

2. The system of claim 1, wherein the third dimension is smaller than a minor diameter of the anti-rotation section.

3. The system of claim 1, wherein the upper tapered section is defined by a chamfer on the internal bore.

4. The system of claim 1, wherein the internal shoulder is located proximal of the tapered first section of the abutment.

5. A dental implant system, comprising:
a screw having a screw head and a threaded end portion;
a dental implant comprising:
   an implant proximal end;
   an internal bore extending distally from the implant proximal end, the internal bore including an upper tapered section, an anti-rotation section having a non-round shape and including at least one planar surface, a lower section having a dimension that is smaller than a dimension of the anti-rotation section, and a threaded section distal of the lower section, the anti-rotation section being located between the upper tapered section and the lower section;
   an external surface including an external-threaded section, a portion of the anti-rotation section being located distal to a proximal end of the external-threaded section; and
a unitary abutment for attachment to the dental implant comprising:
   a post for being located outside of the implant and having a post proximal end and a distal end, the post having an outwardly tapering exterior surface at the distal end, the outwardly tapering exterior surface tapering outwardly in a direction from the implant toward a proximal end of the abutment, the post further having a prosthesis-supporting exterior surface above the outwardly tapering exterior surface, the prosthesis-supporting exterior surface being configured to support a prosthesis, the prosthesis-supporting exterior surface having a length that is greater than a length of the outwardly tapering exterior surface;
   a stem for being located inside of the implant and extending from the distal end of the post, the stem including:
      a first conically tapered section including a first dimension and being received in the upper tapered section of the internal bore of the implant;
      a second section having a non-round cross-sectional shape adapted to rotationally lock with the anti-rotation section of the dental implant, the second section including a second dimension that is smaller than the first dimension of the tapered first section, the second section being located distal to the first section;
      a third section for assisting insertion of the abutment into the implant, the third section being located distal to the second section, the third section having a cylindrical shape;
   a through-bore extending along a longitudinal axis of the abutment; and
   an internal shoulder integrally formed within the abutment and partially defining the through-bore;
      wherein the abutment is inhibited against axial movement distally and proximally relative to the implant when the abutment is axially retained on the dental implant with the first conically tapered section of the stem of the abutment received in the upper tapered section of the internal bore of the implant by the screw passing through the through-bore of the abutment, the screw head seating on the shoulder of the abutment, and the threaded end portion of the screw threadably engaging the threaded section of the internal bore of the dental implant.

6. The dental implant system of claim 5, wherein the second section of the stem includes at least one groove.

7. The dental implant system of claim 5, wherein the non-round shape of the second section includes at least one projection.

8. The dental implant system of claim 5, wherein the first conically tapered section is adjacent to the distal end of the post.

9. The dental implant system of claim 5, wherein the internal shoulder is located proximal of the first conically tapered section of the abutment.

10. The dental implant system of claim 1, wherein the through-bore of the abutment is non-threaded from the proximal end of the abutment to a distal end of the abutment.

11. The dental implant system of claim 1, wherein the abutment includes an engagement surface that engages a corresponding surface of the implant when the abutment is axially retained on the implant.

12. The dental implant system of claim 11, wherein the engagement surface is a surface distal of the tapering section of the abutment and the corresponding surface of the implant is a table at the proximal end of the implant.

13. The dental implant system of claim 11, wherein the engagement surface is transverse to the longitudinal axis of the abutment.

14. The dental implant system of claim 1, wherein the first dimension is a diameter at a distal end of the tapered first section of the abutment and the second dimension is a major diameter of the anti-rotation section of the abutment.

15. The dental implant system of claim 5, wherein the through-bore of the abutment is non-threaded from the proximal end of the abutment to a distal end of the abutment.

16. The dental implant system of claim 5, wherein the abutment includes an engagement surface that engages a corresponding surface of the implant when the abutment is axially retained on the implant.

17. The dental implant system of claim 16, wherein the engagement surface is a surface distal of the outwardly tapering section of the post and the corresponding surface of the implant is a table at the implant proximal end of the implant.

18. The dental implant system of claim 16, wherein the engagement surface is transverse to the longitudinal axis of the abutment.

19. The dental implant system of claim 5, wherein the first dimension is a diameter at a distal end of the first conically tapered section of the stem and the second dimension is a major diameter of the second section of the stem.

\* \* \* \* \*